US008570650B2

(12) United States Patent
Dougherty et al.

(10) Patent No.: US 8,570,650 B2
(45) Date of Patent: Oct. 29, 2013

(54) METHOD AND SYSTEM FOR FAST THREE-DIMENSIONAL STRUCTURED-ILLUMINATION-MICROSCOPY IMAGING

(75) Inventors: William M. Dougherty, Kenmore, WA (US); Steven Charles Quarre, Woodinville, WA (US)

(73) Assignee: Applied Precision, Inc., Issaquah, WA (US)

(*) Notice: Subject to any disclaimer, the term of this patent is extended or adjusted under 35 U.S.C. 154(b) by 364 days.

(21) Appl. No.: 12/964,708

(22) Filed: Dec. 9, 2010

(65) Prior Publication Data

US 2011/0194175 A1 Aug. 11, 2011

Related U.S. Application Data

(60) Provisional application No. 61/285,166, filed on Dec. 9, 2009.

(51) Int. Cl.
*G02B 21/06* (2006.01)
*G02B 21/24* (2006.01)

(52) U.S. Cl.
CPC .............. *G02B 21/06* (2013.01); *G02B 21/24* (2013.01)
USPC ........................................ 359/385; 359/368

(58) Field of Classification Search
USPC ................ 359/368–390, 618, 489.08–489.09
See application file for complete search history.

(56) References Cited

U.S. PATENT DOCUMENTS

| 4,060,323 | A | * | 11/1977 | Hirayama et al. | 355/60 |
| 5,621,561 | A | * | 4/1997 | Belfatto et al. | 359/205.1 |
| 5,748,812 | A | * | 5/1998 | Buchin | 385/18 |
| 2007/0146714 | A1 | | 6/2007 | Mohanty et al. | |
| 2008/0018966 | A1 | | 1/2008 | Dubois et al. | |

OTHER PUBLICATIONS

PCT/US2010/059779—International Search Report—Jul. 22, 2011.

* cited by examiner

*Primary Examiner* — Thong Nguyen

(57) ABSTRACT

A structured-illumination module included in a 3D-structured-illumination-based fluorescence microscope, the structured-illumination module comprising: a structured-illumination-module frame; a beam-alignment module including a central tilt mirror coupled to an underside of a top horizontal plate of the structured-illumination-module frame; a set of directional mirrors, one of which receives, at a given point in time, input, polarized, coherent light reflected from the central tilt mirror; three sets of beam splitters, on three arms of the structured-illumination-module frame, the each splits an incident illumination beam, reflected to the set of beam splitters from a directional mirror of the set of directional mirrors, into a coherent beam triplet; and a phase-shift module that receives a beam triplet, at a given point in time, generated by one of the sets of beam splitters and reflected from the beam-alignment module and that introduces a desired relative phase relationship among the beams of the beam triplet.

1 Claim, 38 Drawing Sheets

STRUCTURED ILLUMINATION SCHEMATIC

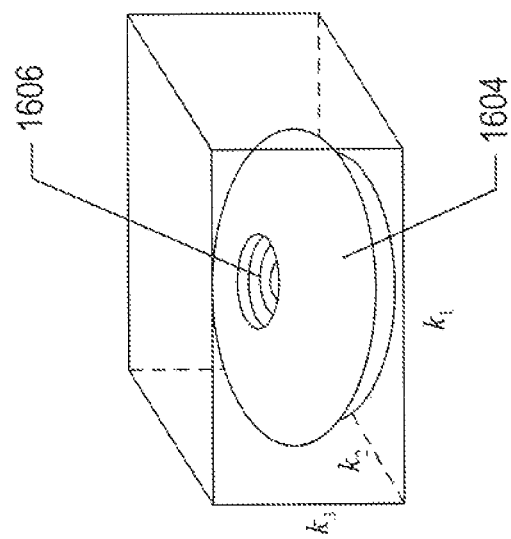
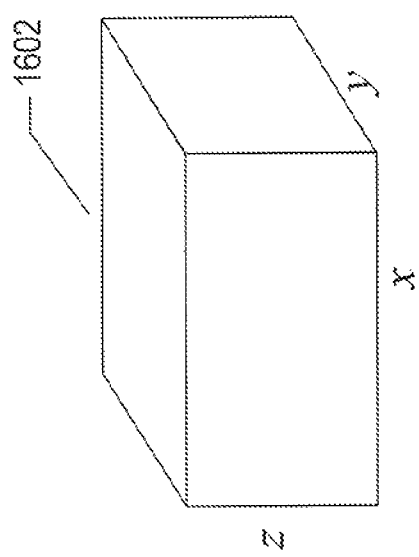
FIG. 16

STRUCTURED ILLUMINATION SCHEMATIC

New Figure XY
Phase_Plot.bmp
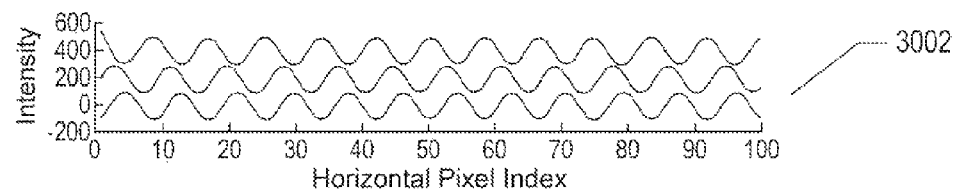
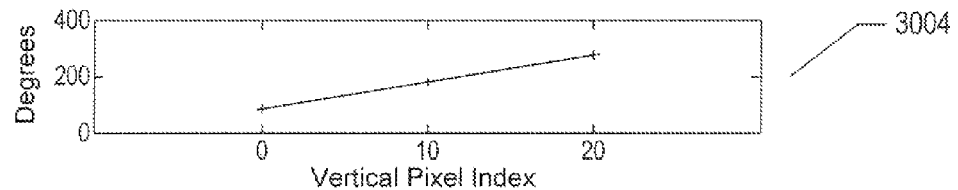
Angle:  12.199 degrees
Pitch:  8.313 ± 0.0039 pixels
FIG. 30

METHOD AND SYSTEM FOR FAST THREE-DIMENSIONAL STRUCTURED-ILLUMINATION-MICROSCOPY IMAGING

CROSS-REFERENCE TO RELATED APPLICATION

This application claims the benefit of Provisional Application No. 61/285,166, filed Dec. 9, 2009.

TECHNICAL FIELD

The present invention is related to fluorescence microscopy and, in particular, to an optical-electrical-mechanical method and subsystem for fast image collection for 3D-SIM imaging.

BACKGROUND

Three-dimensional structured illumination microscopy ("3D-SIM") achieves a factor of two improvement in lateral and axial resolution compared to conventional wide-field fluorescence microscopes used in cell biology. 3D-SIM requires no specialized fluorescent dyes or proteins, unlike certain competing super-resolution techniques. Biologists achieve high resolution with 3D-SIM, but retain convenient and familiar fluorescence labeling techniques. Multiple images of the subject are made with a shilling and rotating illumination pattern. Higher resolution is achieved by solving a system of equations to restore the fine spatial detail normally blurred by diffraction.

A currently-available commercial 3D-SIM instrument uses a linearly polarized laser beam that is split into three orders by a binary phase grating. The three diffracted orders (0-th and $\pm 1^{st}$, respectively) are focused onto the back focal plane of the microscope objective, and combine to form a three-dimensional interference fringe pattern in the sample volume. 3D-SIM data are acquired by taking a fluorescence image excited by the fringe pattern, moving the grating a fifth of a period, approximately five micrometers, then taking another image, and repeating these steps for a total of five images. The grating is then rotated by 60 degrees, and the five image process is repeated, followed by another rotation and another five images, for a total of 15 images per z-step, where a z-step is a fixed point in the z-axis, coincident with the optical axis passing through the objective. Typically, at least eight z-steps are desired, for a total of 120 images per stack. These images are used to solve a system of linear equations to recover a 3D optically sectioned image with approximately double the resolution obtained by conventional wide-field microscopy. The image acquisition times involved are appreciable. Laser exposure may span 5-100 ms, camera readout may span about 50 ms per full-frame, grating motion and settlings may span tens of milliseconds, and rotation of the grating/polarizer assembly may span roughly one full second, leading to a 3D-SIM stack acquisition time of 10-20 seconds.

SUMMARY

Embodiments of the present invention are directed to providing and controlling illumination for three-dimensional structured illumination microscopy. Three phase-coherent beams, referred to as a "beam triplet," are produced with planar beamsplitters. The relative phases of the beams are controlled by piezo-coupled mirrors or other means. The beams pass through the microscope objective and interfere to produce the 3D structured illumination pattern. The spatial orientation and location of the pattern is manipulated by adjusting the relative phases of the beams.

BRIEF DESCRIPTION OF THE DRAWINGS

FIG. 16 illustrates the volume of spatial-frequency domain, or reciprocal space, accessible to a conventional optical system attempting to image a real-space sample volume.

FIG. 30 shows an updating MatLab display used in tuning a 3D-SIM according to one embodiment of the present invention.

DETAILED DESCRIPTION

Embodiments of the present invention are directed to devices and apparatuses that provide for fast 3D-SIM imaging, including a structured-illumination module ("SIM") included within, or added to, a 3D-SIM instrument to produce three-dimensional illumination patterns, the position and orientation of which are controlled by electro-optical-mechanical control features of the SIM discussed below. In an initial subsection, provided below, a brief overview of Fourier optics is provided. Those familiar with Fourier optics may wish to directly proceed to the following subsection, in which embodiments of the present invention are described.

Overview of Fourier Optics

Figure 1:
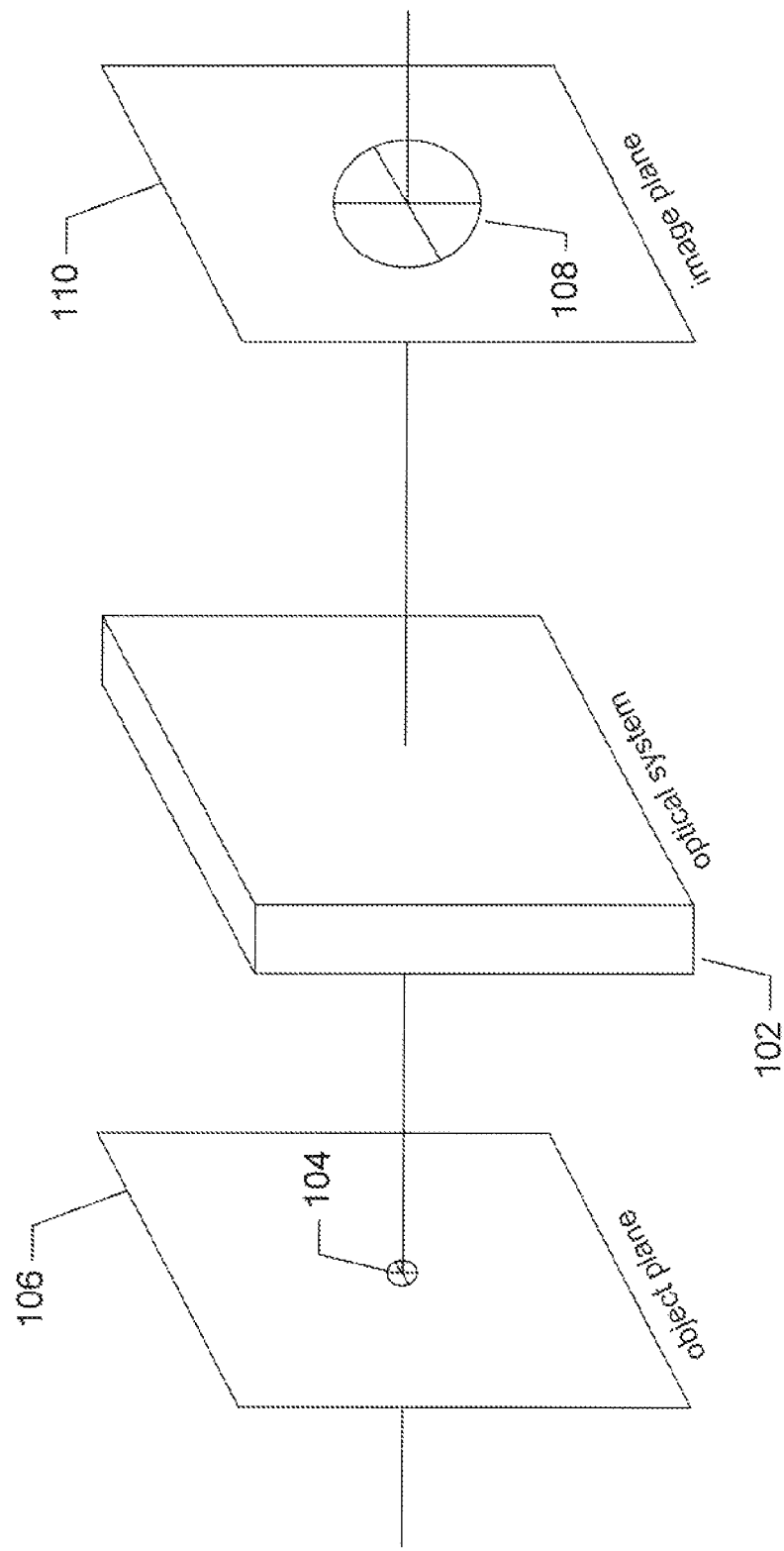
FIG. 1 provides an abstract representation of an optical system, such as a standard optical microscope or fluorescence microscope.

FIG. 1 provides an abstract representation of an optical system, such as a standard optical microscope or fluorescence microscope. In general, the optical system 102 focuses and magnifies an input image 104 within the object plane 104 to form a magnified image 108 on an image plane 110. The object plane is, in microscopy, generally a plane normal to the optical axis within a sample and the image plane, also normal to the optical axis, is generally a CCD detector, the retina of a human eye, or an image plane within another type of detector.

Figure 2:
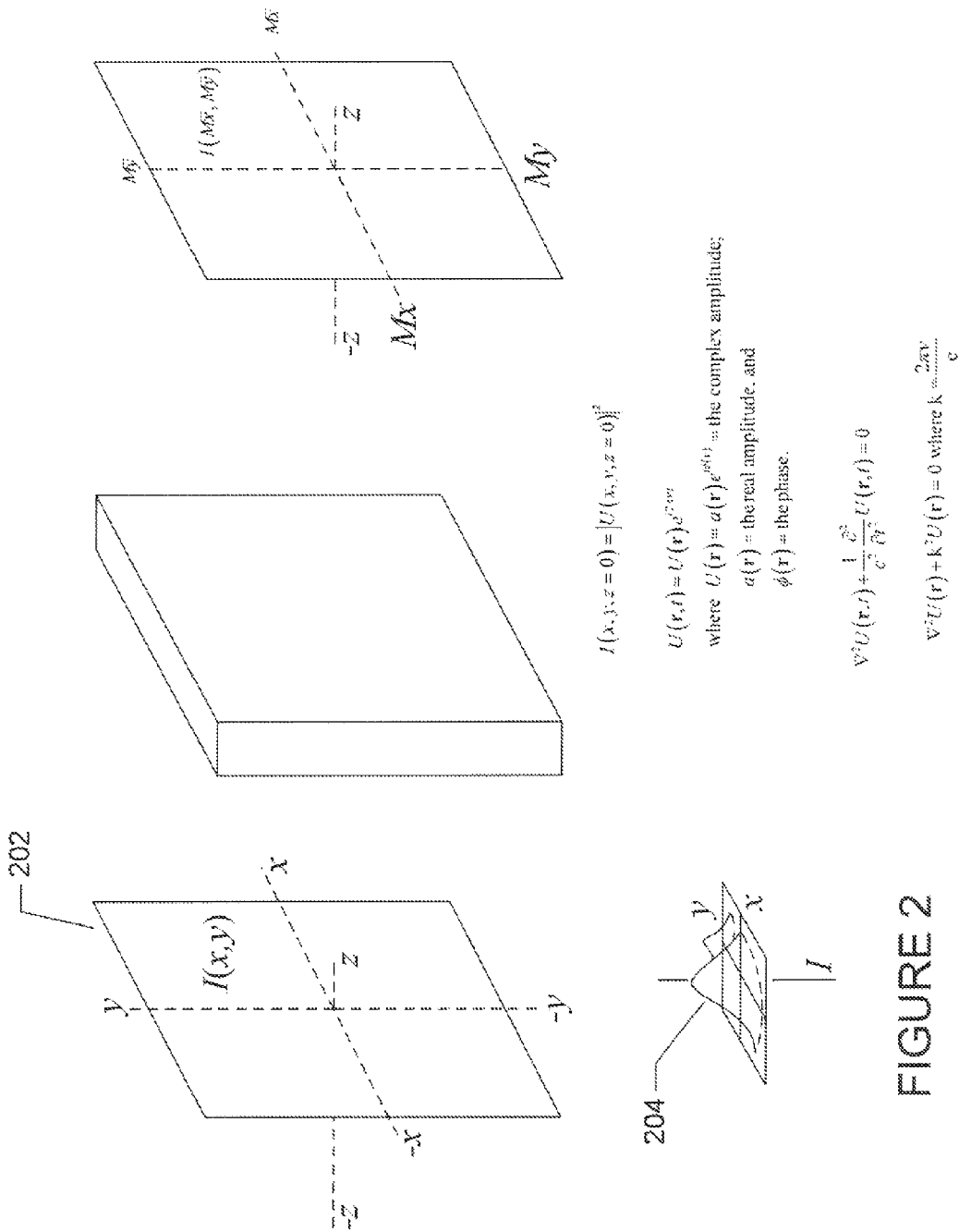
FIGS. 2-4 illustrate a mathematical model for optical imaging.
Figure 3:
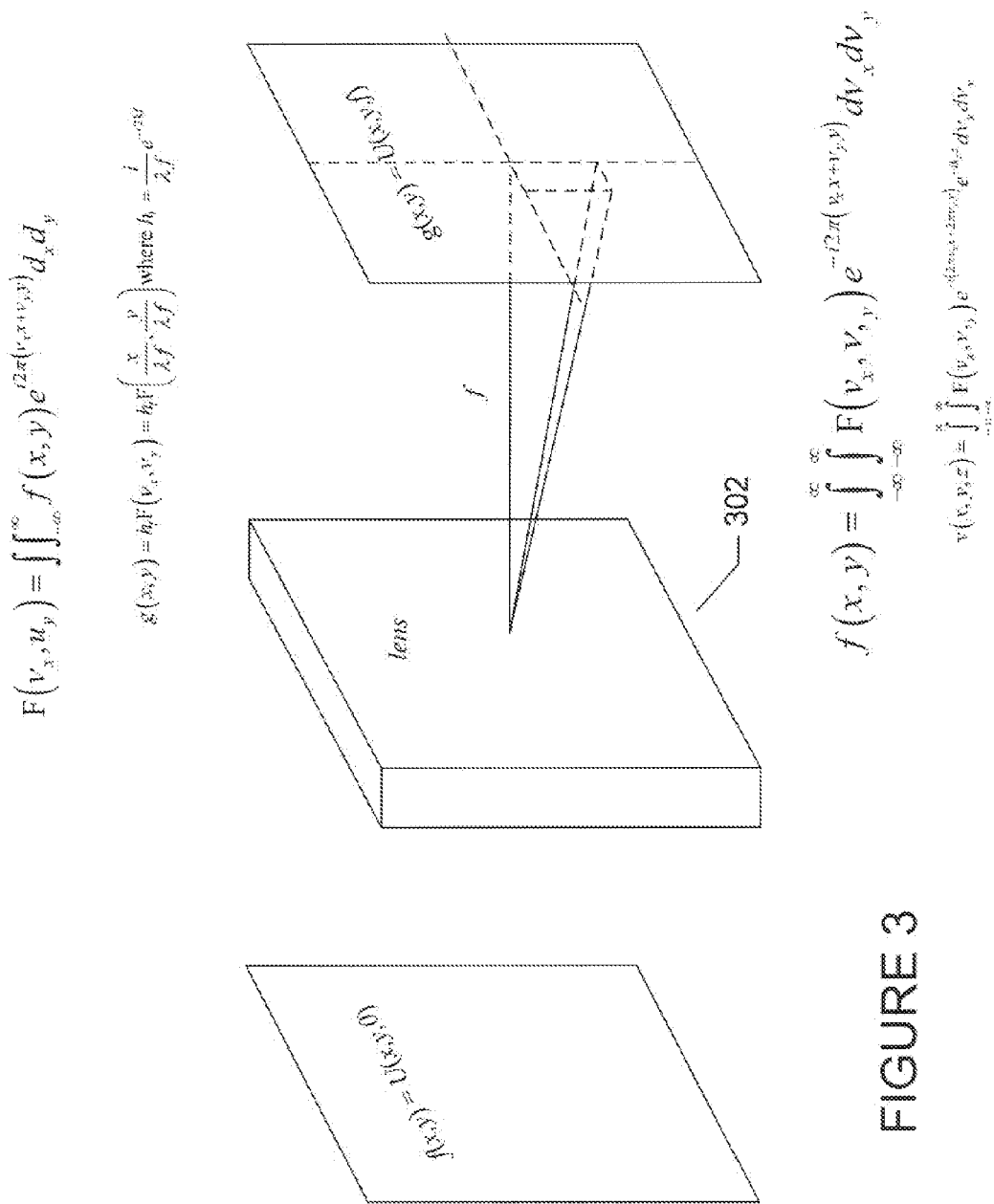
Figure 4:
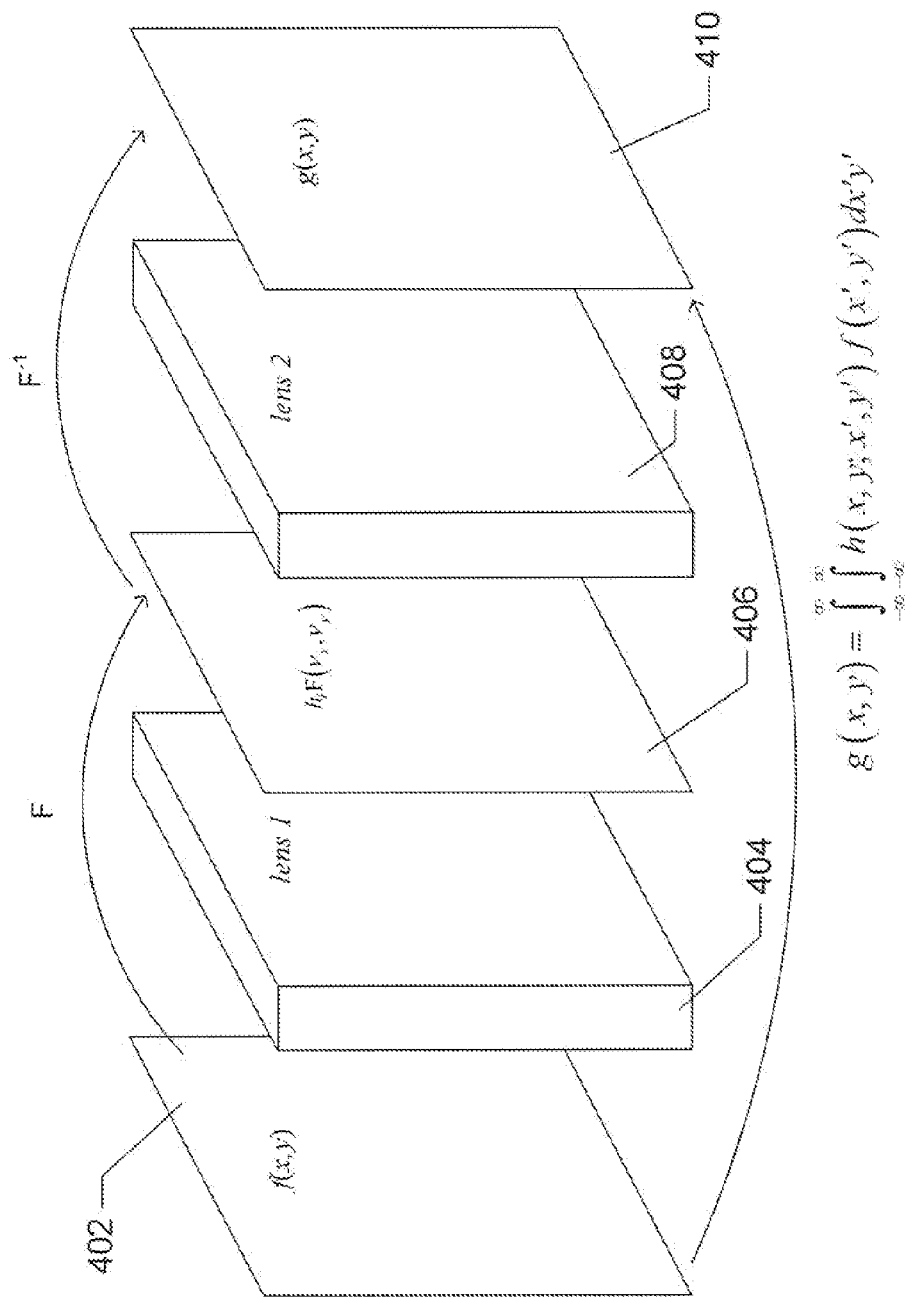

FIGS. 2-4 illustrate a mathematical model for optical imaging. FIGS. 2-4 use the same illustration conventions, or similar illustration conventions, as used in FIG. 1. As shown in FIG. 2, the input image at the object plane 202 can be described as a function $I(x,y,z=0)$ where x and y are orthogonal dimensions in the image plane and z corresponds to the optical axis normal to the image plane and optical-system components. The value of the function $I(x,y)$ represents the intensity of light at each point in the object plane, and can be thought of as a surface 204. The input image, $I(x,y,z=0)$ can be mathematically modeled as the squared magnitude of a wave function:

$$I(x,y,z=0)=|U(x,y,z=0)|^2$$

The wave function can be expressed, in vector form, for monochromatic light of frequency v, as:

$$U(r,t)=U(r)e^{i2\pi vt}$$

where $U(r)=a(r)e^{i\phi(r)}$=the complex amplitude;

a (r)=the real amplitude, and $\phi(r)$=the phase.

The function $U(r,t)$ is a function that satisfies a differential equation known as the "wave equation:"

$$\nabla^2 U(r,t) + \frac{1}{c^2}\frac{\partial^2}{\partial t^2}U(r,t) = 0$$

and a differential equation known as the "Helmholtz equation:"

$$\nabla^2 U(r) + k^2 U(r) = 0$$

where $$k = \frac{2\pi v}{c}$$

$U(r)$ is the time-invariant complex amplitude for the light wave and $U(r,t)$ is a time-dependent model of the light wave. The image $I(x,y)$ is time invariant, depending only on the complex amplitude $U(r)$. The wave function is a scalar function of position and time, and is therefore not a complete mathematical for light, but is adequate for explaining many optical phenomena.

As shown in FIG. 3, a lens 302 can be modeled as an optical system that transforms an input function $f(x,y)=U(x,y,0)$ to an output function $g(x,y)=U(x,y,f)$. The input function $f(x,y)$ and output function $g(x,y)$ are equivalent to the time-independent wave functions for a light wave at the object plane and image plane, respectively. The input function $f(x,y)$ can be modeled as a superposition of harmonic functions of the spatial dimensions x and y:

$$f(x,y) = \int_{-\infty}^{\infty}\int_{-\infty}^{\infty} F(v_x, v_y)e^{-i2\pi(v_x x+v_y y)} dv_x dv_y$$

The coefficients $F(v_x,u_y)$ are obtained by the Fourier transform:

$$F(v_x,u_y)=\iint_{-\infty}^{\infty}f(x,y)e^{i2\pi(v_x x+v_y y)}d_x d_y$$

The operation of a lens on the input function $f(x,y)$ to produce the output function $g(x,y)$ can be expressed as:

$$g(x,y) = h_l F(v_x, v_y) = h_l F\left(\frac{x}{\lambda f} \cdot \frac{y}{\lambda f}\right)$$

where $h_l = \frac{i}{\lambda f} e^{-i2kf}$

In other words, the output image is a frequency-domain image generated by focusing harmonic components of the input image $f(x,y)$ to different points in the output image $g(x,y)$. The output image $g(x,y)$ is a Fourier transform of the input image $f(x,y)$.

FIG. 4 illustrates a mathematical model for an imaging optical system. An input image 402 is transformed, by a first lens 404 to a frequency-domain image 406, as discussed above, and a second lens 408 transforms the frequency-domain image 406 to a final, spatial-domain output image $g(x,y)$ 410 by a process modeled as a second, inverse Fourier transform. The entire process can be more mathematically modeled as a convolution:

$$g(x,y) = \int_{-\infty}^{\infty}\int_{-\infty}^{\infty} h(x,y;x',y')f(x',y')dx'y'$$

where $h(x,y;x',y')$ is the impulse-response function for the optical system. As discussed in greater detail below, the output image can be computed as a convolution of the impulse-response function with the input image. Note that, for an optical system that magnifies the input image, input-image coordinates x' and y' correspond to output-image coordinates x=x'M and y=y'M, where M is the magnification factor.

Figure 5:
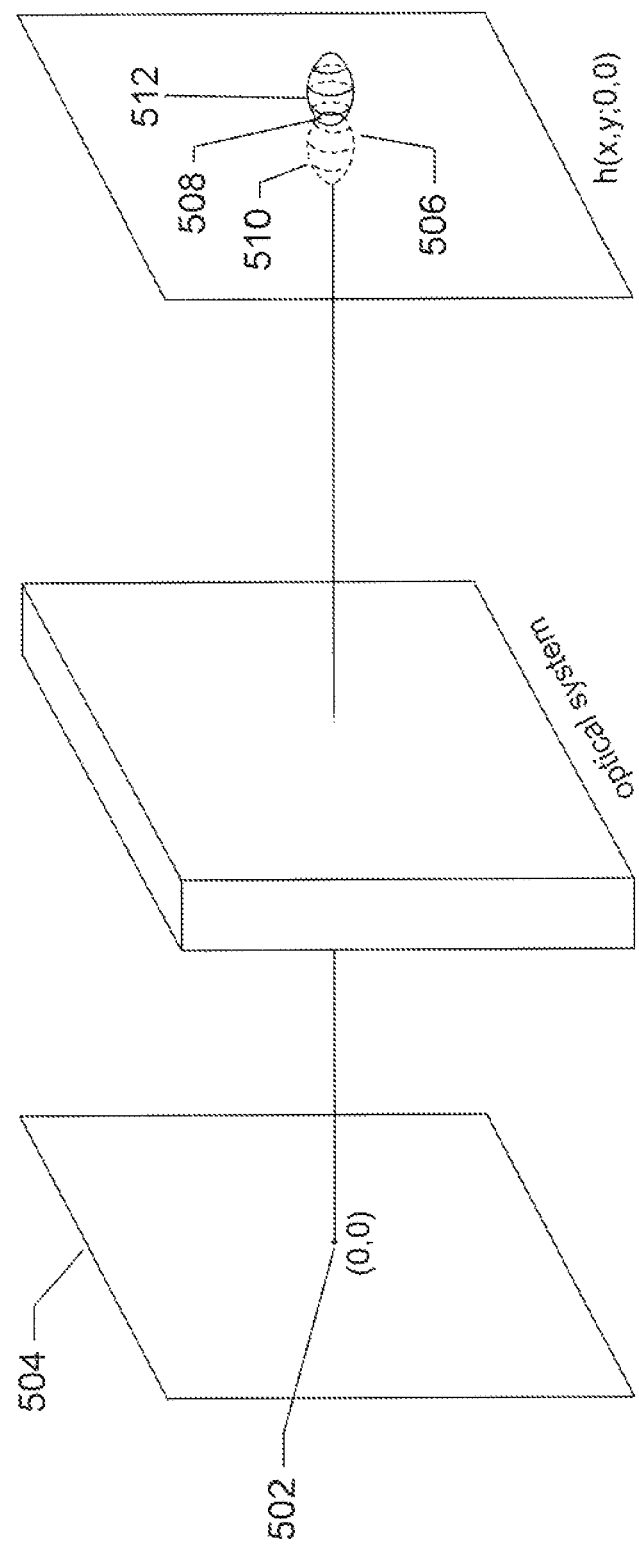
FIGS. 5-8 illustrate characteristics of the impulse-response function h(x, y; x', y') discussed with reference to FIG. 4, above.

FIGS. 5-8 illustrate characteristics of the impulse-response function $h(x,y;x',y')$ discussed with reference to FIG. 4, above. As shown in FIG. 5, the impulse-response function $h(x,y;0,0)$, corresponding to the point (0,0) 502 on the object plane 504, is a two-lobed intensity distribution 506 with circular cross-section 508 in the image plane, a first lobe 510 of the two-lobed distribution is cylindrically symmetric about the z-axis and projects from the image plane back toward the object plane, and the second lobe 512, also cylindrically symmetric about the optical axis, projects outward, away from the object plane from the circular cross-section 508 in the image plane. In FIG. 5, and in subsequent figures, the illustrated surface of the impulse-response function is a surface of constant intensity. The idealized impulse-response function extends without hound through real space. However, at a particular distance in any direction from the point (0,0) in output-image space, the intensity of the input-response function falls to an arbitrarily low value, so that, for example, a constant-intensity surface can be constructed to describe the impulse-response function for an intensity level below which intensity is undetectable. The impulse-response function can be considered to be a function that maps a point source in the object plane to an intensity distribution in output-image space, or, alternatively, as the image of the point source. The output image becomes increasingly unfocused with distance, in the z direction, from the image plane. Blurring of the image of the point source with distance is reflected in the initial increase in the radii of circular cross-sections of the impulse-response function with increasing distance from the output-image plane. Subsequent decrease in the radii of circular cross-sections with greater distance from the image plane is related to the decreasing intensity with distance from the origin (0, 0) in the image plane.

Figure 6:
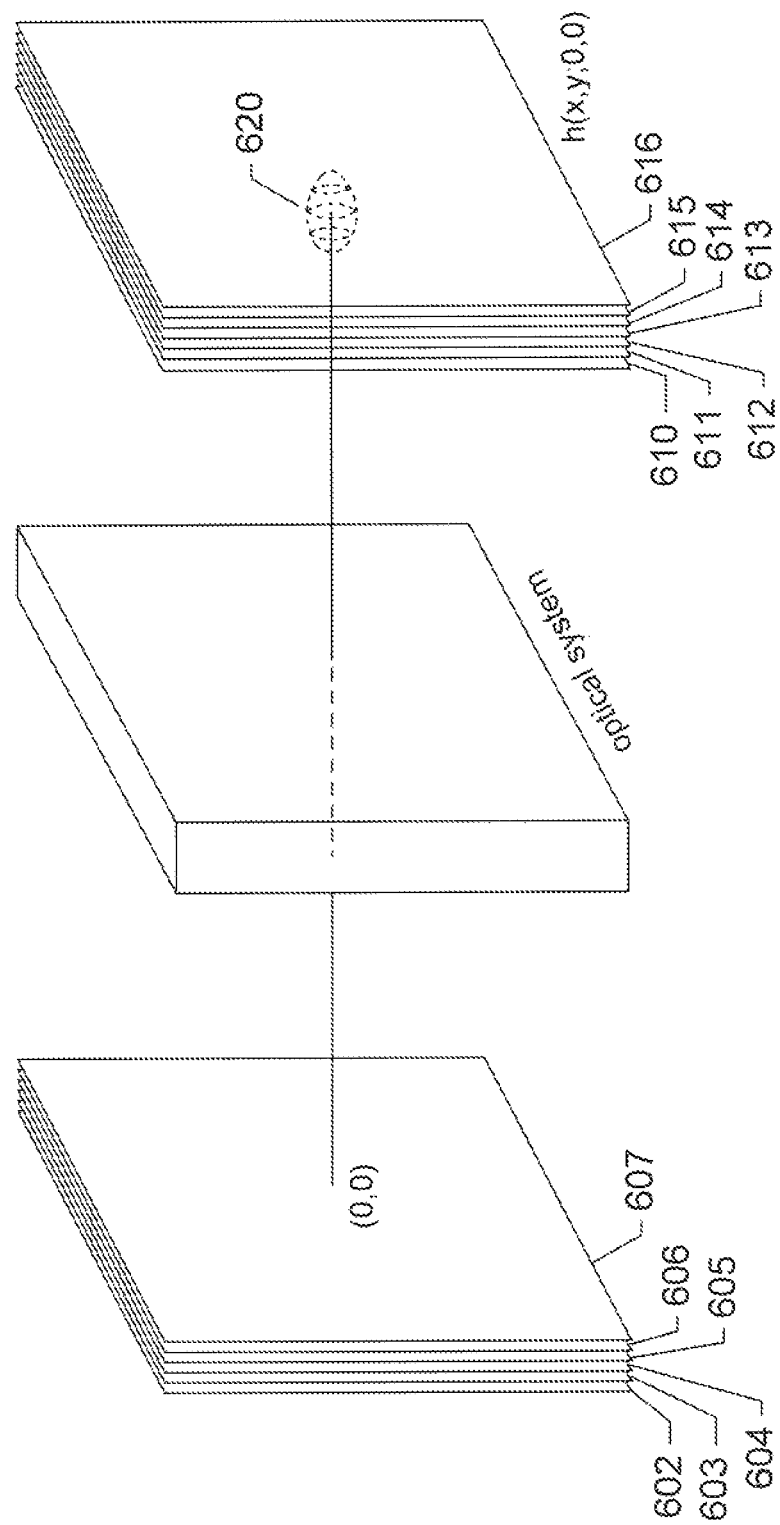

FIG. 6 illustrates a constant-intensity surface of the impulse-response function in three-dimensional output-image space. As shown in FIG. 6, fluorescence microscopists commonly image a series of object planes 602-607 within a sample by changing the distance between the sample and the objective lens after acquiring each image of the series of images at a fixed position with respect to the objective. This produces a corresponding set of output images 610-616. When a set of input images about the point (0, 0, 0) in three-dimensional input-image space is imaged by the optical system, the three-dimensional impulse-response function corresponding to the point (0, 0, 0) is a cylindrically symmetrical ellipsoid 620 in three-dimensional output-image space. In an aberration-free optical system with continuous imaging in the x, y, and z directions, the impulse-response function h(x, y; 0, 0) is spherically symmetric about the point (0, 0, 0) in output-image space. Again, the impulse-response function extends outward from the point (0, 0, 0) in output-image space through all of real space. However, the intensity decreases with increasing distance from the point (0, 0, 0), so that an ellipsoid or sphere of constant intensity can be constructed to represent the impulse-response function.

Figure 7:
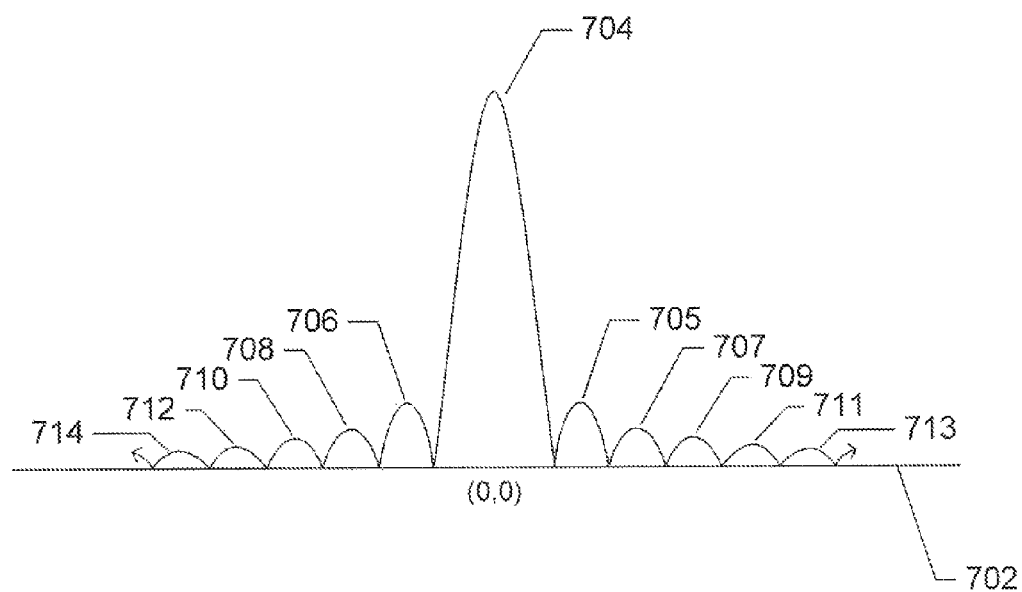
Figure 8:
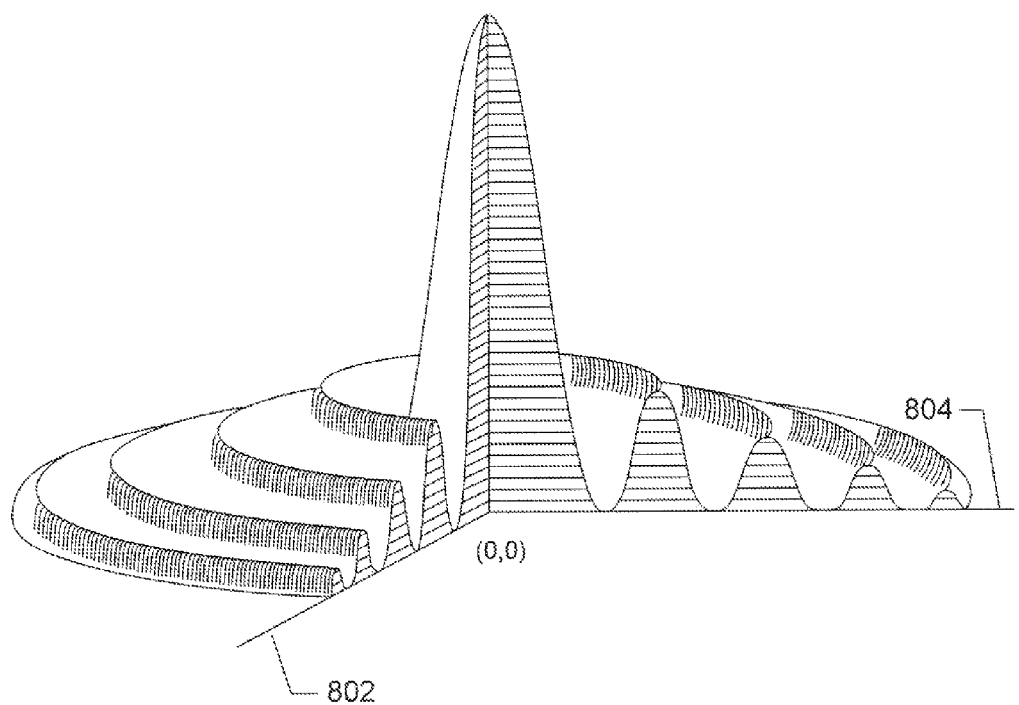

FIG. 7 illustrates the impulse-response function in one dimension within the output-image plane. The horizontal axis 702 is a line in the output-image plane passing through the origin (0, 0). The theoretical impulse-response function has a tall, relatively narrow central peak 704 with secondary peaks of decreasing height 705-714 extending in both directions away from the central peak. The height of the impulse-response curve corresponds to intensity and the horizontal axis 702 corresponds to linear distance from the origin in the output-image plane. The theoretical impulse-response function is proportional to the square of the $J_1$ Bessel function. FIG. 8 provides a representation of the impulse-response function in three-dimensional space, where the two horizontal axes 802 and 804 lie in the plane of the output-image plane and cross at the origin (0, 0) and the height, at any point on the surface of the impulse-response function corresponds to the intensity observed at a corresponding position on the image plane. An image of the impulse-response function produced by an optical system appears to be a central bight disk, corresponding to the central peak of the impulse-response function, with concentric rings of increasing radius corresponding to the rings or ridges surrounding the central peak.

Figure 9:
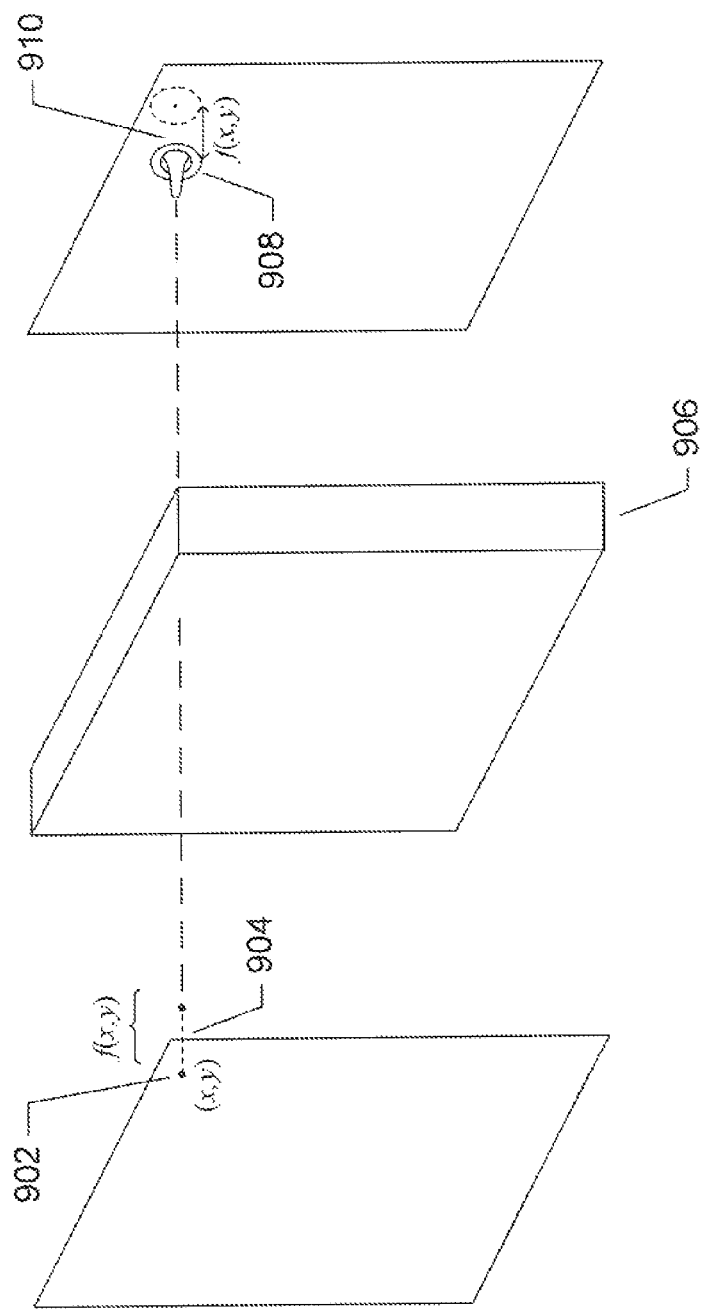
FIGS. 9-10 illustrate a convolution-based mathematical model, discussed above with reference to FIG. 4, for computing an output image of an optical system from the image input to the optical system and the impulse-response function for the optical system.
Figure 10:
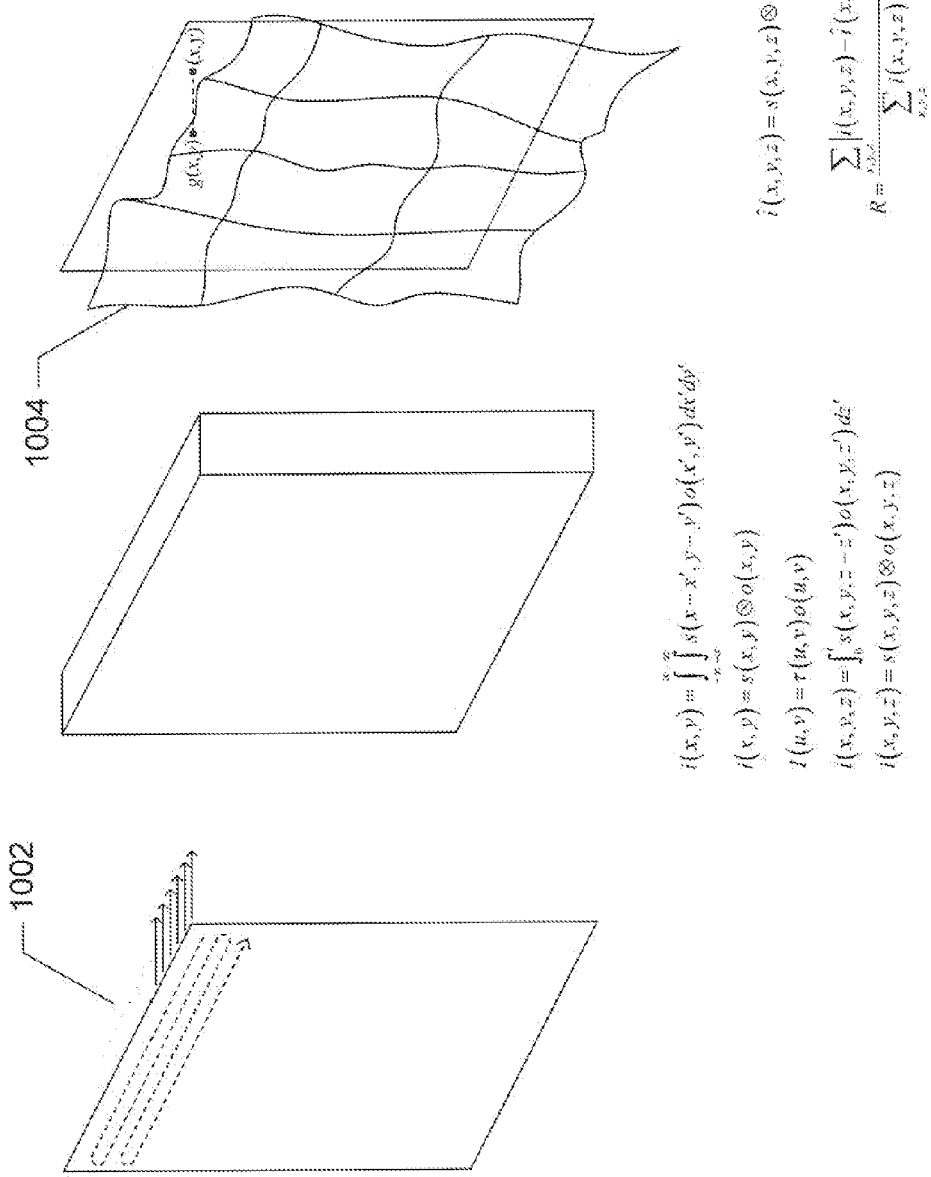

FIGS. 9-10 illustrate a convolution-based mathematical model, discussed above with reference to FIG. 4, for computing an output image of an optical system from the image input to the optical system and the impulse-response function for the optical system. Note that the impulse-response function illustrated in FIGS. 5-8 is a theoretical impulse-response function of an aberration-free optical system. However, in all practical implementations of optical systems, it is not possible to compute an impulse-response function for the system, due to many complex aberrations that are difficult to mathematically model. The impulse-response function is experimentally determined by imaging tiny light sources in the object plane. It should also be noted that, in practical systems, the impulse-response function may vary with respect to location of point sources in the input-image plane. However, in the following discussion, the impulse-response function is generally assumed to be position independent.

FIG. 9 illustrates the basic operation that is repeated over the entire area of the input image plane in order to compute the output image by the convolution method discussed above with reference to FIG. 4. A given point (x, y) 902 in the input-image plane, to which a wave-function amplitude ƒ(x, y) 904 corresponds, is regarded as a point source of light of amplitude ƒ(x, y), light emitted from which passes through the optical system 906 and is transformed by the optical system into the corresponding impulse-response function 908 multiplied by the amplitude ƒ(x, y) 910. As shown in FIG. 10, when the basic operation show in FIG. 9 is repeated for all points in the input-image plane 1002, the sum of all the input-response functions generated by a light source at each point forms a surface 1004, where the height of the surface g(x, y) above a corresponding point (x, y) in the output-image plane is the intensity of the output image at that point. Thus, changing notation, the output image i(x, y) is computed as convolution of the impulse-response function, or point-spread function ("PSF"), s(x–x', y–y'), with the input image o(x', y'). In mathematical notation:

$$i(x, y) = \int_{-\infty}^{\infty}\int_{-\infty}^{\infty} s(x-x', y-y')o(x', y')dx'dy'$$

$$i(x, y) = s(x, y) \otimes o(x, y)$$

This convolution operation becomes a multiplication operation in the frequency domain:

$$I(u,v) = \tau(u,v)o(u,v)$$

where I(u,v) is the frequency-domain transform of the output image i(x,y); τ(u,v) is the optical transfer function that is the Fourier transform of the PSF; and O(u,v) is the frequency-domain transform of the input image o(x,y). When three-dimensional imaging is considered, these relationships can be expressed as:

$$i(x,y,z) = \int_0^z s(x,y,z-z')o(x,y,z')dz'$$

$$i(x,y,z) = s(x,y,z) \otimes o(x,y,z)$$

In deconvolution microscopy, an estimate of the input image o(x,y,z), ô(x,y,z), is convolved with the PSF to produce a corresponding computed image î(x, y, z):

$$\hat{i}(x,y,z) = s(x,y,z) \otimes \hat{o}(x,y,z)$$

In general, convolution is carried out in the frequency domain, by a multiplication operation, and the corresponding frequency-domain entities are then transformed, by inverse Fourier transforms, back to their spatial-domain equivalents. An R factor, or residual, can be computed to reflect the difference between the computed image and the observed image:

$$R = \frac{\sum_{x,y,z}|i(x, y, z) - \hat{i}(x, y, z)|}{\sum_{x,y,z} i(x, y, z)}$$

The estimated input image can then be altered, by any of various techniques, such as a Newton-descent optimization technique, to produce a subsequent, better estimate of the input image, from which a corresponding output image can be computed and a new R factor generated. The process is iterated until the R factor falls below a threshold value, indicating that the estimated input image sufficiently closely represents the actual image input to the optical system.

Figure 11:
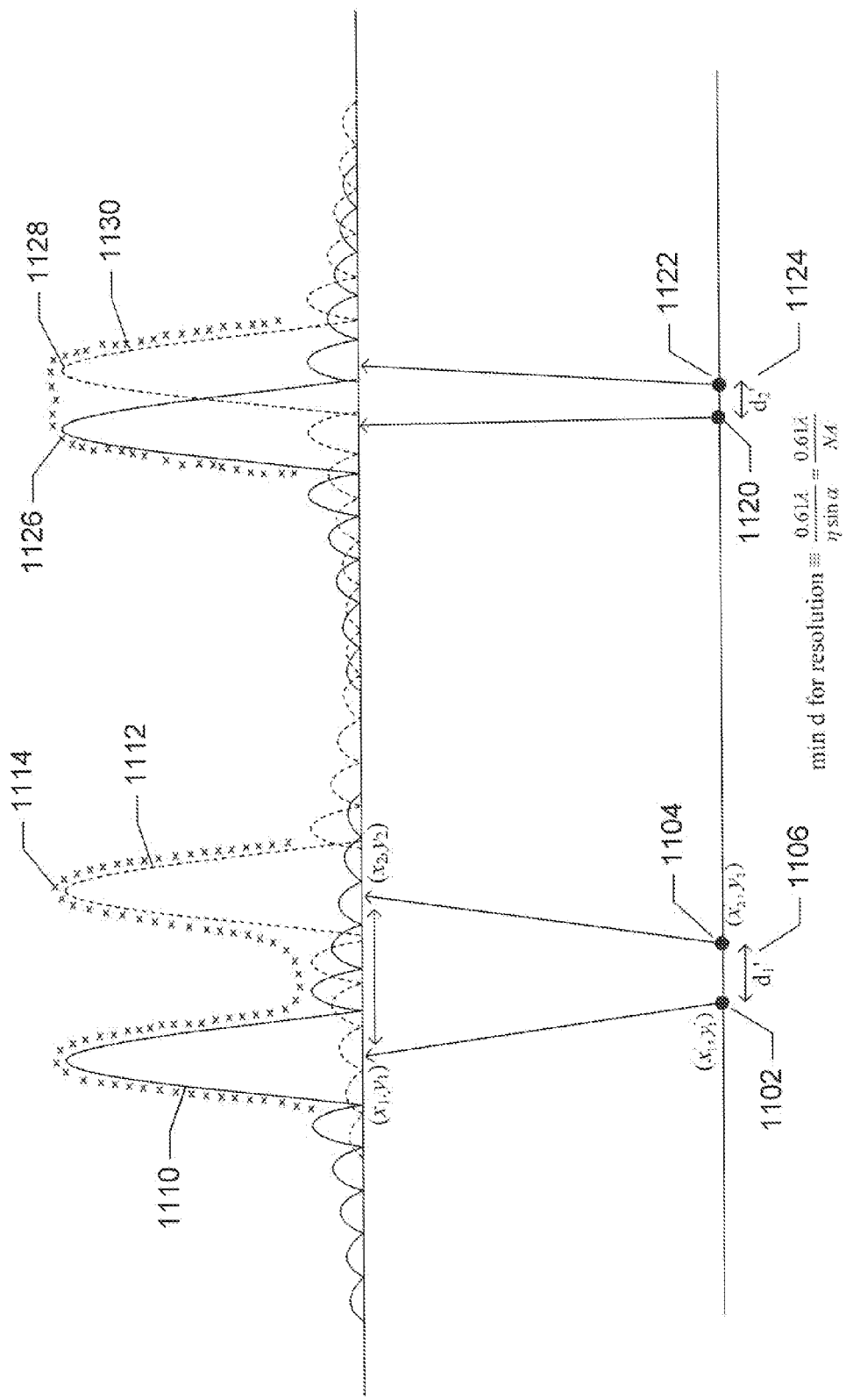
FIG. 11 illustrates the diffraction limit associated with of optical microscopy.

FIG. 11 illustrates the diffraction limit associated with of optical microscopy. Consider two points $(x'_1, y'_1)$ 1102 and $(x'_2, y'_2)$ 1104 in the object plane separated by distance $d_1'$ 1106. The images of these two points output from an optical system are two point-spread functions 1110 and 1112 centered at the output-image points $(x_1, y_1)$ and $(x_2, y_2)$ corresponding to points $(x'_1, y'_1)$ and $(x'_2, y'_2)$. The spreading of light from point sources of the input image into point-spread-function images at the output image is a diffraction-related phenomenon. When $d_1'$ is sufficiently large that the corresponding distance between the centers of the point-spread functions $d_1$ in the output image separates the point-spread-function distributions so that the sum of the two point-spread functions, represented in FIG. 11 by curve 1114, remains clearly bimodal, the images of points 1102 and 1104 in the output image can be distinguished from one another. However, when two points 1120 and 1122 in the input image are separated by a sufficiently small distance $d'_2$ 1124 that the images of the two points 1126 and 1128 in the output image overlap, with the sum of the two point-spread functions, represented by curve 1130 in FIG. 11, merging into a single peak, the two points 1120 and 1122 cannot be distinguished from one another in the output image. The minimum spacing, or maximum resolution, for traditional optical microscopy is generally regarded as:

$$\frac{0.61\lambda}{\eta\sin\alpha} = \frac{0.61\lambda}{NA}$$

where $\lambda$ is the wavelength of light; and
NA is the numerical aperture for the optical system.
The minimum spacing in the input image corresponds to spacing between output point-spread functions at which the first left-hand zero point of the right-hand point-spread function coincides with the first right-hand zero point of the left-hand point-spread function. The minimum separation of features that can be imaged corresponds to approximately 200 nm for optical microscopy systems. The minimum spacing, or maximum resolution, is referred to as "the diffraction limit," since the point-spread-function images of point sources in the output image arise as a result of diffraction.

Figure 12:
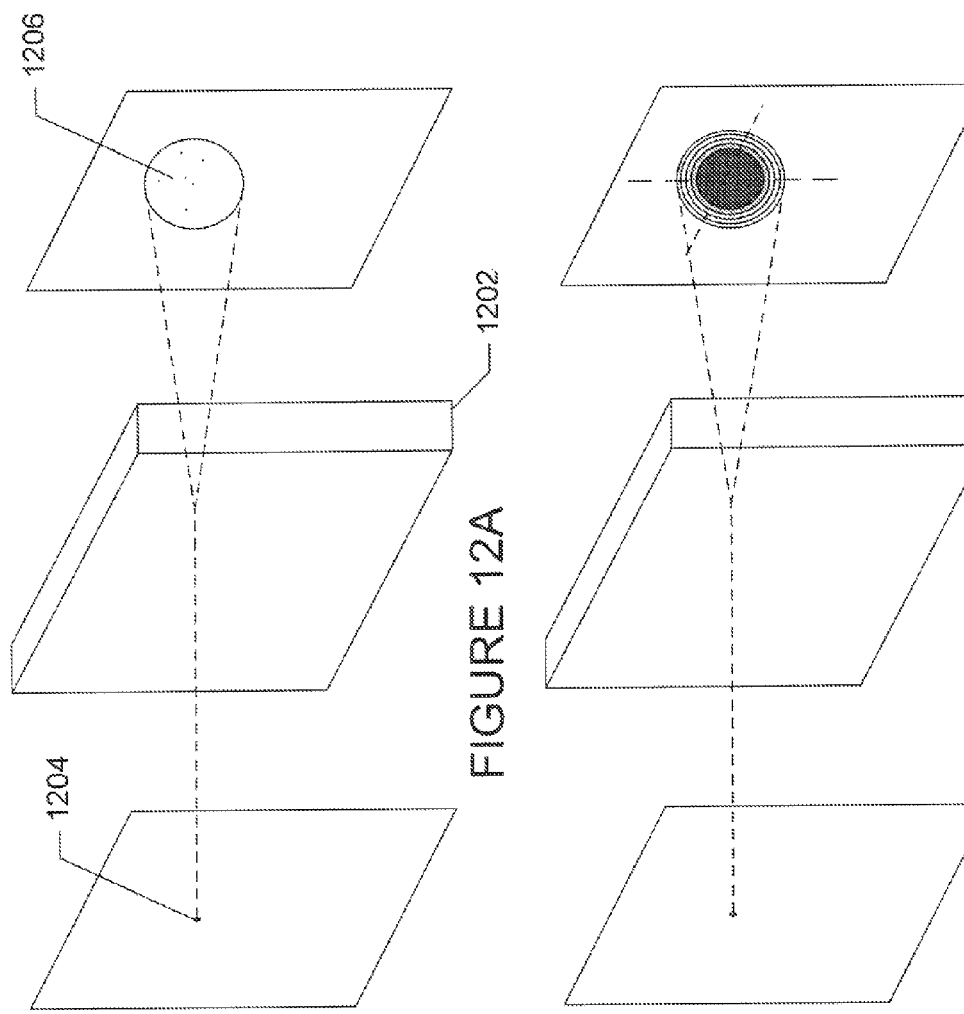
FIGS. 12A-B illustrate a basis for super-resolution microscopy.

Until the 1990's, the diffraction limit discussed with reference to FIG. 11 was considered to be an absolute resolution limit for optical microscopy. However, during the past 20 years, various super-resolution fluorescence-microscopy techniques have been developed. FIGS. 12A-B illustrate a basis for super-resolution microscopy. FIG. 12A illustrates the effect of an optical system 1202 on light emitted in the direction of the z axis from a point 1204 on the object plane. As discussed above, the optical system spreads the intensity of the light over a disk-shaped point-spread function 1206 in the image plane. The point-spread function is thus viewed as a real-time smearing, or diffusion, of a point source by the optical system in output-image space. This smearing of point-like source light occurs for a number of different reasons. One important reason is that optical components, such as lenses, have finite apertures, and thus receive only a lower-angle portion of the non-coherent light emitted from a point source. Higher-angle emitted light rays fall outside the disk of a lens, and thus fall outside the optical path. The higher-angle rays that fail to be admitted to the optical components correspond to higher-frequencies in the frequency domain. Thus, optical components act as a spatial-frequency filter. Focusing of light by a second lens, modeled as an inverse Fourier transform, produces a spatial-domain image that is somewhat blurred, due to removal of high-frequency frequency-domain signals by optical components. Many additional factors contribute to dispersion of light in an output image represented by the point-spread function, including various types of aberrations inherent in optical components and other factors.

As illustrated in FIG. 12B, a second way to consider the point-spread function is that the point-spread function represents a probability distribution, with the intensities associated with points by the point-spread function corresponding to probabilities that individual photons will be deflected to that point by an optical system. Considered in this way, when a point-like source in the object plane is continuously imaged, and the continuous image accumulated, over time, by an electronic detector, such as a CCD detector, the accumulated intensity in the output image will be distributed according to the point-spread function. The point of highest accumulated intensity, in the output image, can be located to a precision equal to that of the resolution of the detector after accounting for the magnification factor of the optical system, when output light is collected for a sufficient period of time to generate a well-formed distribution of accumulated intensity in the image plane. This point corresponds to the object-plane location of a point source corresponding to the PSF in the image plane. It is theoretically possible to determine the location of point sources, using the centroids of corresponding PSF distributions in an output image, to a resolution of 1 nm or greater resolution. However, in order to achieve such precision, the light-emitting point sources must be separated by sufficient distance that their point-spread-function images, in the output image, do not appreciably overlap. Thus, while the location of sparsely distributed fluorophores can be determined to sub-diffraction-limit resolution, the fluorophores must be positioned within the sample so that the distance between any two fluorophores is greater than the diffraction-limit distance of between 180 and 200 nm, according to currently-practiced super-resolution imaging techniques.

EMBODIMENTS OF THE PRESENT INVENTION

Figure 13:
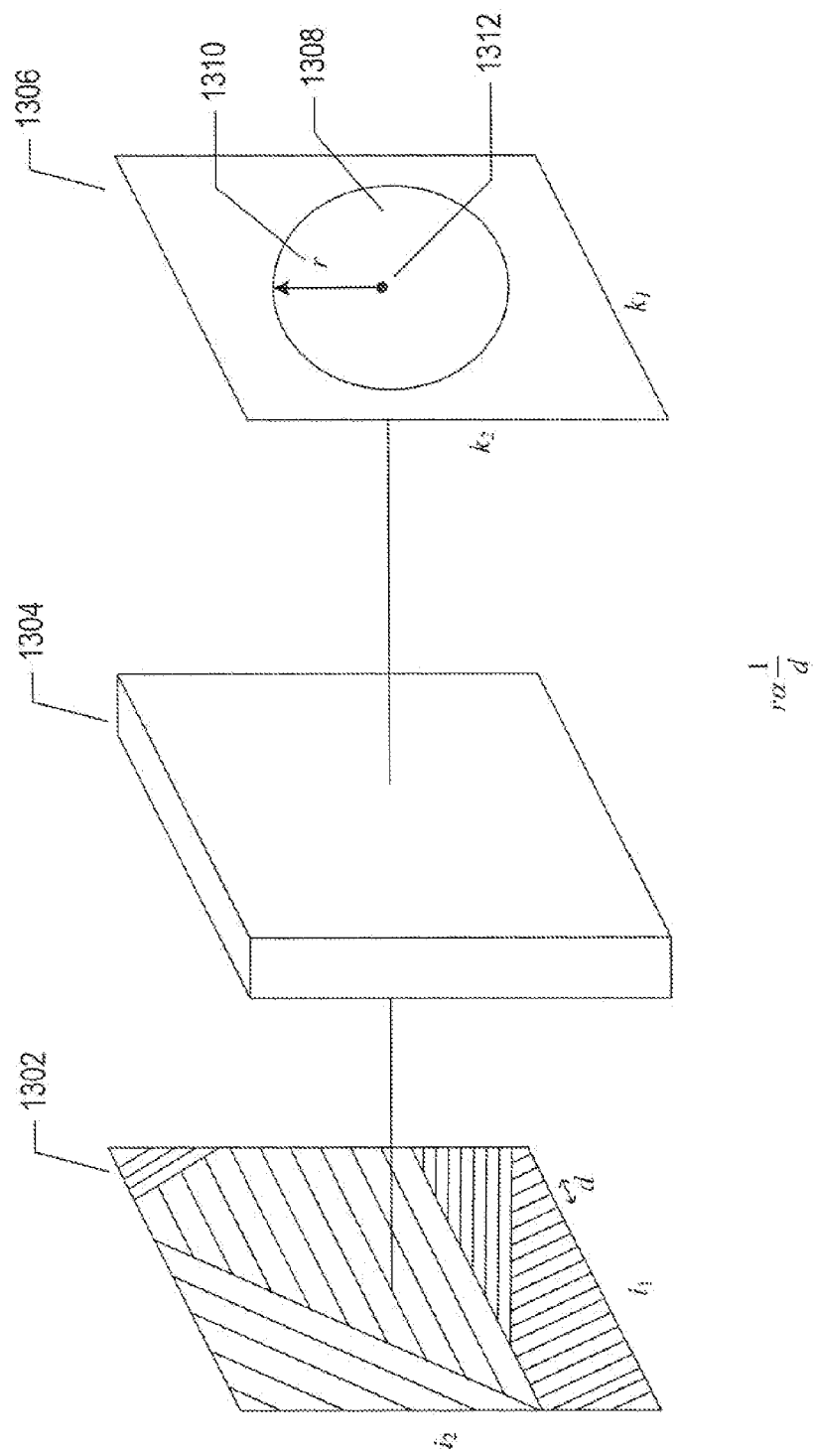
FIG. 13 illustrations relationships between the spatial domain and the spatial-frequency domain.
Figure 14:
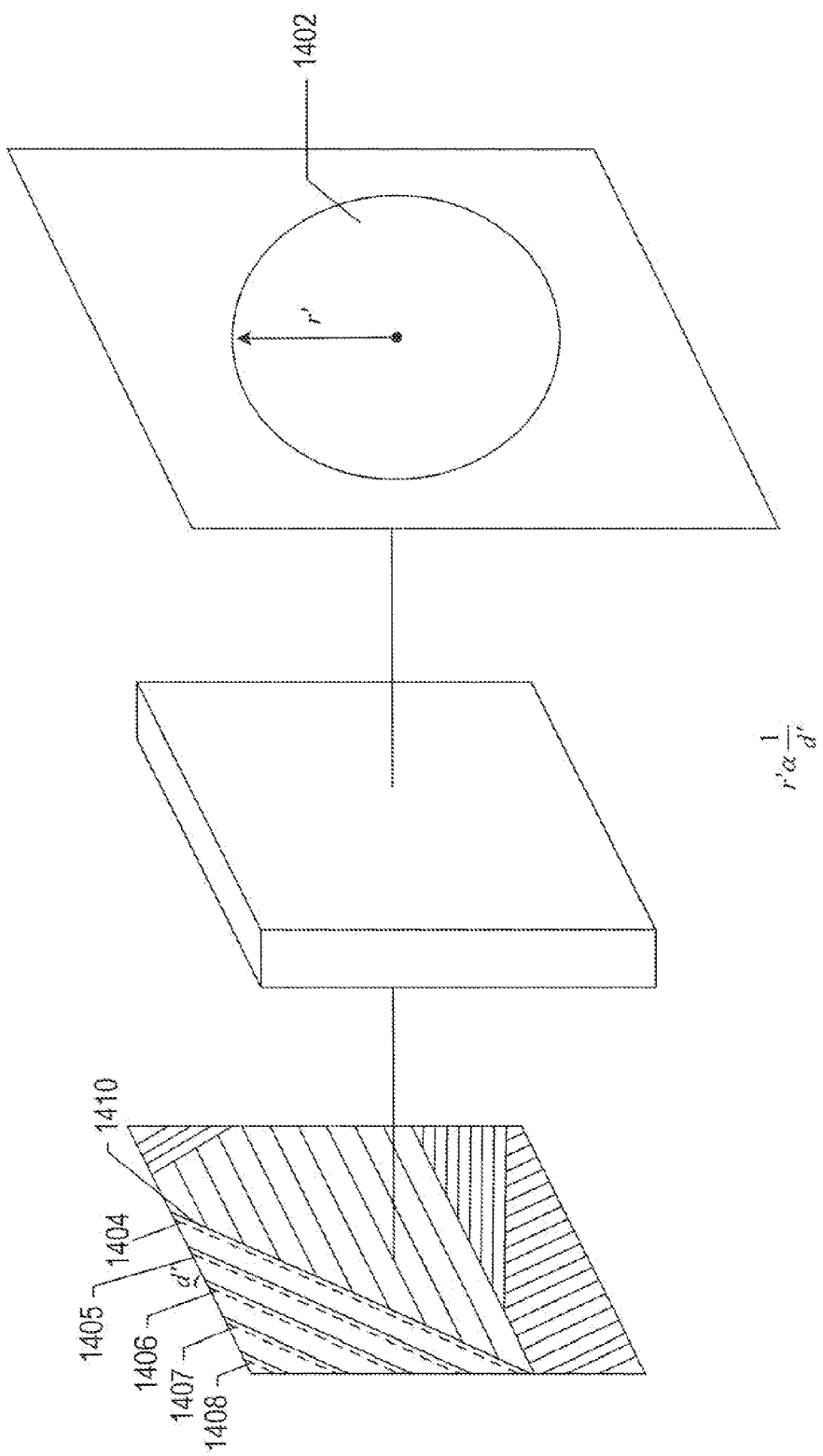
FIG. 14, which uses the same illustration conventions as FIG. 13, illustrates one approach to increasing the resolution of a fluorescence microscope.

FIG. 13 illustrations relationships between the spatial domain and the spatial-frequency domain. In FIG. 13, which uses similar illustration conventions used in FIGS. 1-12, an object or sample being imaged by a fluorescence microscope is considered to be in a real, spatial domain 1302. When fluorescent light is emitted by fluorophores in the object, or sample, the emitted fluorescent light passes through an optical lens 1304 to produce a Fourier transform of the image in a spatial-frequency domain 1306. Because of the limitations of the optical system and the diffraction limit associated with imaging of spatial-domain sample features, the signal produced by the lens in the spatial-frequency domain 1306 is confined to a disk-like region 1308 with a radius r 1310, where r is inversely related to d, the smallest distance between two features that can be resolved by the optical system. In other words, the distances of positions of spatial-frequency-domain signals from the intersection of the optical axis with the spatial-frequency-domain plane 1312 is inversely related to, or reciprocal, to spacings between features in the spatial-domain fluorescence-emission pattern. FIG. 14, which uses the same illustration conventions as FIG. 13, illustrates one approach to increasing the resolution of a fluorescence microscope. Were it possible to access a larger region of the spatial-frequency domain 1402, show in FIG. 14 with a radius r' larger than the radius r, shown in FIG. 13, then a Fourier transform of the expanded spatial-frequency domain would provide spatial-domain information about more closely spaced features, in the sample, than can be imaged by the optical system using conventional techniques. For example, a sample, shown in FIGS. 13 and 14 to have patterns of light and dark lines of different orientations, may include a set of lines 1404-1408, shown as dashed lines in FIG. 14, that are too closely spaced to the neighboring solid lines, such as solid line 1410, to be imaged by the optical system shown in FIG. 13. However, were the larger region of spatial-frequency domain 1402 accessible to the optical system, then the information contained in that larger region could be transformed, by an inverse Fourier transform, to produce an image of the sample in which the illumination-pattern features 1404-1408 are resolved.

Figure 15:
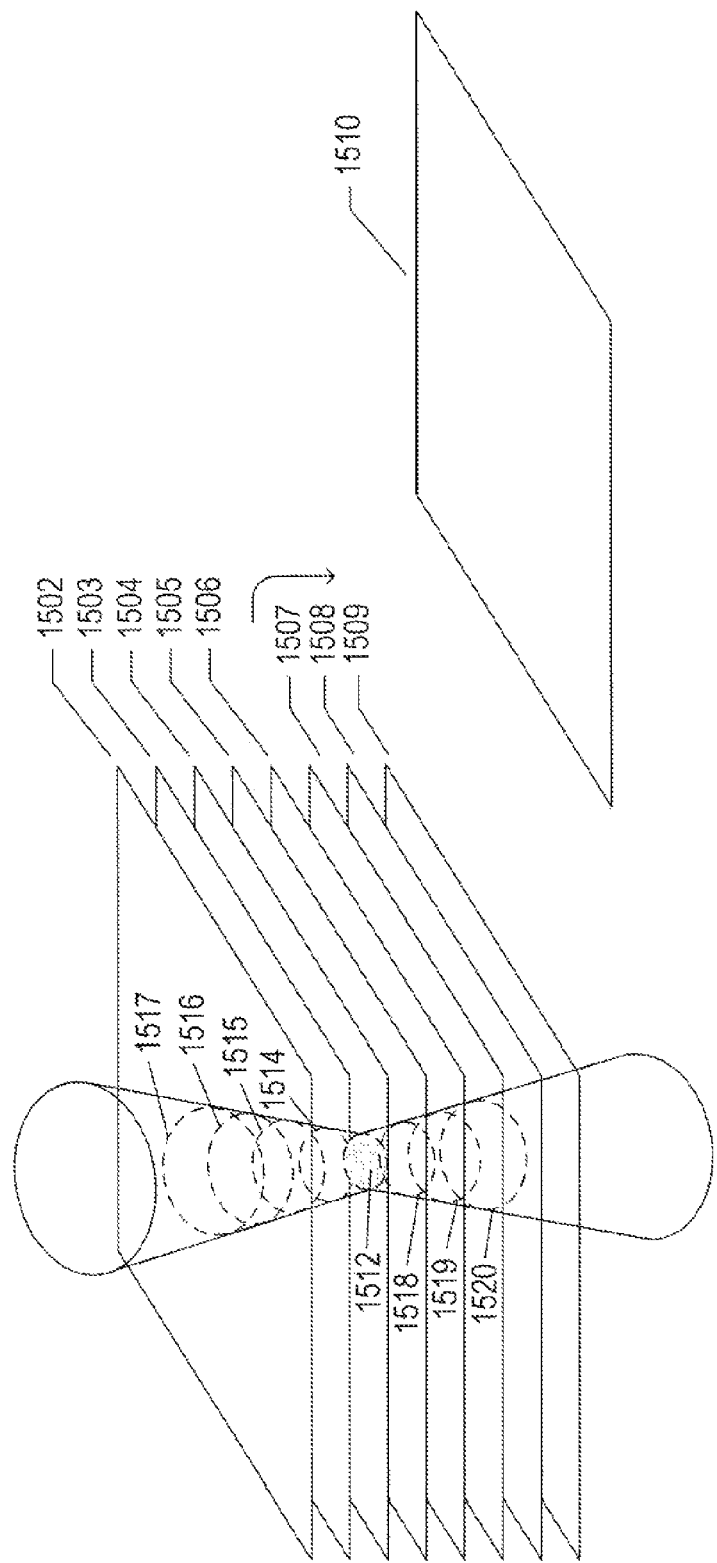
FIG. 15 illustrates a second problem associated with three-dimensional imaging using conventional microscopy.

FIG. 15 illustrates a second problem associated with three-dimensional imaging using conventional microscopy. In three-dimensional imaging, multiple, closely spaced, planar images are recorded for each of multiple closely spaced planes 1502-1509 within a sample volume normal to the z axis, or optical axis. In certain cases, the three-dimensional information may be processed in order to produce a single, higher-resolution two-dimensional image 1510 representative of the central plane of the stack of closely spaced images. Unfortunately, in the z direction, unfocused fluorescent emission from nearby image planes is recorded along with the focused illumination from a particular image plane. For example, as shown in FIG. 15, when the central sample plane 1506 is imaged and, in particular, when fluorescent emission from a particular feature, represented by a shaded disk 1512 within the central sample plane 1506, is imaged, the detector will generally receive unfocused fluorescent emission from nearby sample planes, represented in FIG. 15 by unshaded disks 1514-1517 above the image sample plane and unshaded disks 1518-1520 below the sample plane. This unfocused illumination falls onto the detector along with the focused illumination from the considered feature 1512, leading to an inability to record image information within a region of the sample image surrounding the intersection of the optical axis with the sample plane, and leads to blurring of a surrounding region.

FIG. 16 illustrates the volume of spatial-frequency domain, or reciprocal space, accessible to a conventional optical system attempting to image a real-space sample volume. A real-space sample volume 1602 generally includes emission patterns from fluorophores distributed at microscale and nanoscale dimensions within the real-space sample. However, due to the limitations of the optical system, discussed above with reference to FIGS. 13-15, only a toroidal region 1604 of the spatial-frequency domain is accessible to the optical system. The lack of accessible spatial-frequency-domain information and at greater distances from the origin than the external surface of the torus limits the resolution of features in the sample that can be imaged, and the absence of spatial-frequency-domain signal in the invagination 1606 within the toroidal shape coaxial with the optical axis, referred to as the "missing cone," prevents imaging of portions of the sample domain near to the optical axis.

Figure 17A:
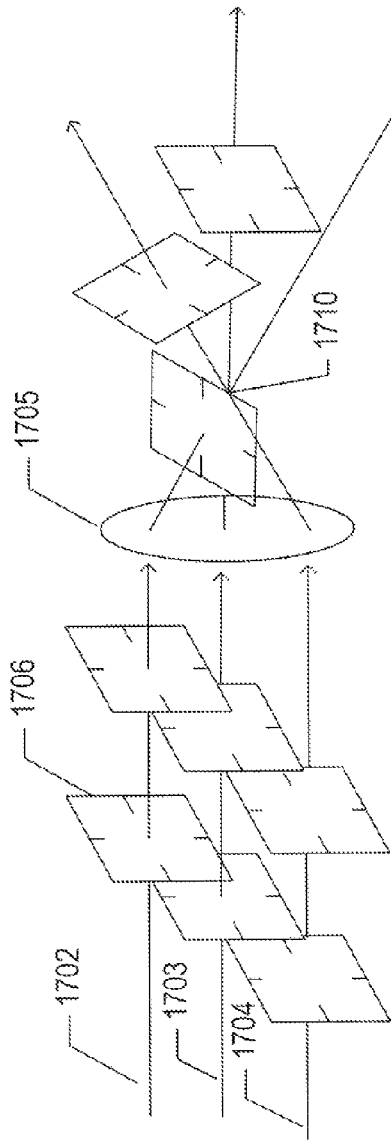
FIGS. 17A-B illustrate generation of a three-dimensional structured-illumination pattern, or grid, using three coherent illumination beams.
Figure 17B:
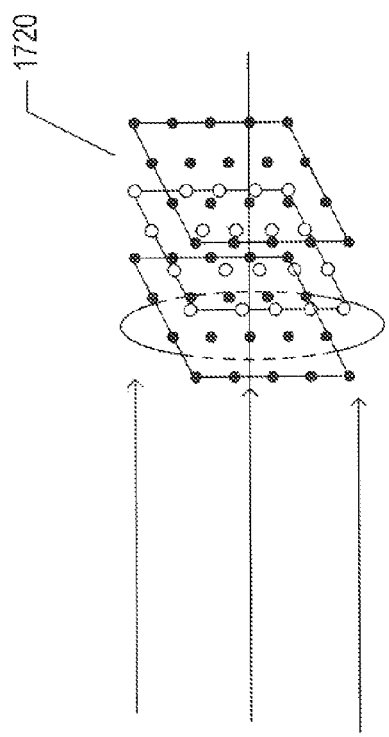

3D-SIM provides a method by which both higher-resolution regions of the spatial-frequency domain as well as inaccessible axial regions of the spatial-frequency domain can be accessed by an optical system. FIGS. 17A-B illustrate generation of a three-dimensional structured-illumination pattern, or grid, using three coherent illumination beams. As shown in FIG. 17A, three coherent beams 1702-1704 are introduced onto the back focal plane of a high magnification, high numerical aperture objective lens 1705. The three coherent beams 1702-1704 are plane waves in which the phases of all component waves of each beam are identical across any plane, such as plane 1706, normal to the beam direction. Although the three incident illumination beams are coherent, each illumination beam may have a different phase displacement than the other two illumination beams. Focusing of the incident beams by the objective lens 1702 to a focal point 1710 changes the direction of the two non-axial illumination beams 1702 and 1704, as shown in FIG. 17A, as a result of which the wave vectors k of the three plane waves are no longer parallel. As a result, the three sets of plane waves intersect to form a grid-like pattern of bright spots, due to constructive interference, and dark surrounding regions, due to destructive interference. In other words, as shown in FIG. 17B, a complex stationary three-dimensional wave 1720 is obtained, which features a three-dimensional lattice of bright, cylindrically elliptical regions at lattice points separated by dark regions. In the SIMs that represent embodiments of the present invention, the positions of the grid points and orientation of the lattice axes can be selected by varying the phase relationships of the incident, illumination beams 1702-1704. As explained below, data is recorded for a large number of different positions and orientations of the structured-illumination pattern in order to reconstruct a three-dimensional image for a sample volume.

Figure 18:
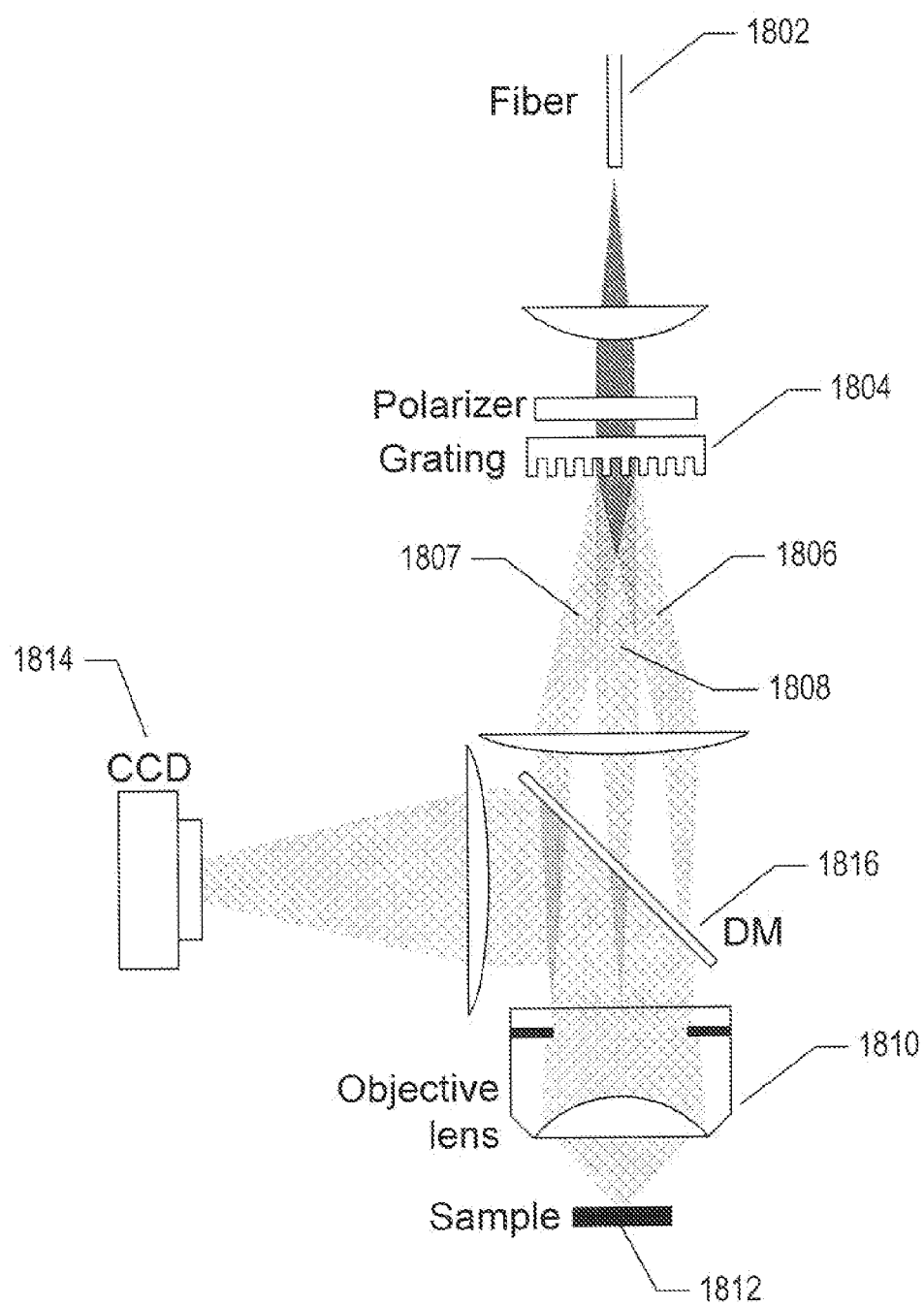
FIG. 18 illustrates a conventional 3D-SIM apparatus.

FIG. 18 illustrates a conventional 3D-SIM apparatus. Laser light from a multi-mode fiber 1802 is collimated onto a linear phase grading 1804. The linear phase grading generates three different illumination beams 1806-1808 as the 1, 0, and +1 order diffracted beams from the linear phase grading. These three illumination beams are refocused onto the back focal plane of the objective lens 1810. They interfere with one another to generate a structured-illumination pattern within a volume of the sample at the focal plane of the objective lens 1812. Fluorescent emission from illuminated fluorophores passes back through the objective lens and is reflected into a CCD camera 1814 via a dichroic mirror 1816 for data collection.

Next, an overview of structured-illumination-based data collection and image reconstruction is provided. Consider an optical system for which the point spread function is H(r). The data observed by the optical system for a fluorophore-labeled and fluorescent-light-emitting sample or object, D(r), is, as discussed in the preceding subsection, a convolution of the spatial distribution of fluorescent emission, E(r) with a point spread function:

$$D(r)=(E \otimes H)(r).$$

The Fourier transform of the observed data is:

$$\tilde{D}(k)=\tilde{E}(k)\tilde{H}(k)=\tilde{E}(k)O(k)$$

where tildes (~) indicate the Fourier transform of the corresponding real-space quantities, $O(k)=\tilde{H}(k)$ is the optical transfer function, and k is a position vector in the spatial-frequency domain.

In fluorescence microscopy, the desired information is the density distribution of fluorophores in the sample, S(r). When the sample is illuminated by an illumination intensity I(r), the distribution of fluorescent emission is given by:

$$E(r)=S(r)=I(r)$$

It should be noted that the above expression, and the expressions that follow, represent simplifications of a more detailed theoretical treatment of structured-illumination-based data collection and image reconstruction. The Fourier transform of the distribution of fluorescent emission is also convolution:

$$\tilde{E}(k)=(\tilde{S}\otimes\tilde{I})(k)$$

When the illumination I(r) is spatially varying, then $\tilde{I}(k)$ is nontrivial, and the convolution operation is nonlocal. In particular, the convolution can make the observed data within the observable region of $\tilde{E}(k)$ depend on normally unobservable components of $\tilde{S}(k)$ from other parts of reciprocal space. That information is then observable, in principle, but must be computationally extracted from image data. In the case that the structured-illumination pattern is the sum of a finite number of components, each of which is separated into an axial and lateral function:

$$I(r_{xy}, z) = \sum_m I_m(z) J_m(r_{xy})$$

where $r_{xy}$ denotes the lateral coordinates (x,y), and each lateral-component function $J_m$ is a simple harmonic wave, and when the axial functions $I_m$ are harmonic or the structured-illumination pattern is fixed, in the axial direction, with relation to the focal plane of the microscope during multiple two-dimensional-image data collection, extraction of the normally unobservable components of $\tilde{S}(k)$ is facilitated. The observed data can then be expressed as:

$$D(r) = \sum_m \int H(r - r') I_m(z - z') S(r') J_m(r'_{xy}) dr'$$

$$= \sum [(HI_m) \otimes (SJ_m)](r)$$

where primed vectors refer to the sample reference frame and the unprimed vectors refer to the instrument reference frame. In the above expressions, m indexes the various component harmonics arising from the periodic structured-illumination pattern. Designating the $m^{th}$ term of the sum as $D_m$, the Fourier transform of $D_m$ is then:

$$\tilde{D}_m(k)=O_m(k)[\tilde{S}(k)\otimes\tilde{J}_m(k_{xy})],$$

where $O_m=O\otimes\tilde{I}_m$ is the Fourier transform of $HI_m$.

It was assumed above that $J_m$ is a simple harmonic, $$J_m(r_{xy})=e^{i(2\pi p_m r_{xy}+\phi_m)}$$

where $p_m$ is the lateral wave vector of component m and $\phi_m$ is a phase displacement for component m, which implies that $\tilde{J}_m(k_{xy})=\delta(k_{xy}-p_m)e^{i\phi_m}$. Substituted into Eq. 6, this implies that each data set obtained from each acquired image of D(r), the Fourier transform of the acquired image of D(r), can be written as:

$$\tilde{D}(k) = \sum_m \tilde{D}_m(k) \sum_m O_m(k) e^{i\varphi_m} \tilde{S}(k - p_m)$$

a sum of a finite number of copies of the object information $\tilde{S}$, each moved laterally in reciprocal space by a distance $p_m$, filtered (and band-limited) by a transfer function $O_m$, and phase-shifted by a phase $\phi_m$. In summary, each lateral frequency component m of the illumination structure corresponds to a separate optical transfer function $O_m$, which is given by a convolution of the conventional detection OTF with the axial illumination structure of the $m^{th}$ pattern component, and applies to a component of object information that has been translated in reciprocal space by the lateral wave vector $p_m$ of that pattern component.

As seen in Eq. 8, a single raw data image is a sum of several different information components, one for each index m. To restore the data, these information components are separated. This can be done by acquiring additional data sets with different known values of the phases $\phi_m$. Changing the phase values by phase shifts $\delta\phi_m$ alters the coefficients $e^{i\phi_m}$ in Eq. 8 from $e^{i\phi_{m0}}$ to $e^{i(\phi_{m0}+\delta\phi_m)}$, leading to a linearly independent combination of the unknown information components. Each phase-shifted image thus supplies one independent linear equation in N unknowns (where N is the number of frequency components in Eq. 8). If data are acquired with at least N different phases, the number of equations is at least equal to the number of unknowns, allowing the N information components to be separated by solving the system of equations via matrix inversion.

In practice, the situation is usually simplified further in several ways. Because physical light intensity is a real-valued function, exponential terms in the lateral function $J_m$ occur in pairs with opposite $p_m$, corresponding to information from symmetrically located regions of reciprocal space. Because the Fourier transform $\tilde{a}(k)$ of any real-valued function a(r) has the symmetry property that $\tilde{a}(-k)$ is the complex conjugate of $\tilde{a}(k)$, only one information component from each such pair needs to be calculated. When the set of different lateral spatial frequencies $p_m$ of the illumination pattern is, in fact, the fundamental frequency and harmonics of a periodic pattern, then all the spatial frequencies are multiples of the fundamental: $p_m=mp$. Furthermore, when phase-shifting of the illumination takes place by spatially translating a rigid pattern, then the phase-shifts $\delta\phi_m$ are also multiples of a fundamental phase-shift: $\delta\phi_m=m\delta\phi$. For patterns with reflection symmetry, the same applies to the starting phases, $\phi_{m0}=m\phi_0$, and thus for the total phase: $\phi_m=m\phi$. In this situation, the observed data can be written as:

$$\tilde{D}_m(k) = \sum_m O_m(k) e^{im\varphi} \tilde{S}(k - mp).$$

The measured data gains normally unobservable spatial-frequency-domain information in two ways: (1) the support of each transfer function $O_m$ is extended axially, compared to the conventional OTF O, through the convolution with the axial function $\tilde{I}_m$; and (2) the translation by nip moves new information laterally into the support of $O_m$.

Because the $O_m$ and $p_m$ are known, the separated information components can be computationally moved back, by a distance $p_m$, to their true positions in reciprocal space, recombined into a single extended-resolution data set, and retransformed into real space. The total effective observable region with this method is given by the support of the convolution of the conventional OTF O with the total illumination structure $\tilde{I}$. The maximal resolution increase in a given dimension is therefore equal to the maximum illumination spatial frequency in that dimension. Since the set of spatial frequencies that can be generated in the illumination is limited by diffraction in exactly the same way as the set of frequencies that can be observed, when the illumination and observation takes place through the same optical system, the maximum possible spatial frequency in the illumination equals the conventional resolution limit of the detection, scaled by the ratio of emission and excitation wavelengths. The maximum resolution extension possible in this matter is therefore a factor of $(1/\lambda_{exc}+1/\lambda_{em})/(1/\lambda_{em})=1+\lambda_{em}/\lambda_{exc}$, slightly more than two, in each dimension. This is true axially as well as laterally.

In convention 3D-SIM instruments, the fluorescent sample is illuminated with three mutually coherent beans of excitation light. In general, a coherent superposition of plane waves with wave vectors $k_j$ produces a total light intensity $$I(r) \propto \left|\sum_j E_j e^{ik_j \cdot r}\right|^2 = \left(\sum_j E_j^* e^{-ik_j \cdot r}\right) \cdot \left(\sum_q E_q e^{-ik_q \cdot r}\right)$$
$$= \left(\sum_{j,q} E_j^* \cdot E_q e^{i(k_q-k_j)\cdot r}\right)$$

which consists of one spatial component at each pairwise difference vector $k_q-k_j$ between any two of the plane-wave propagation vectors. Interference between the three illumination beams thus produces a three-dimensional excitation intensity pattern, 1720 in FIG. 17B, that contains seven Fourier components, one at each difference vector between the three illumination wave vectors. The observable region that becomes accessible with this illumination pattern is the convolution of the seven-dot illumination structure with the conventional OTF support, resulting in an accessible region that lacks the inaccessible missing cone and that is extended along one direction to double resolution with respect to the real-space direction corresponding to that direction. The procedure is repeated with the illumination pattern rotated to other directions in order to obtain general resolution doubling over the spatial-frequency domain.

Parameters are determined for the optical instrumentation by collecting data from a sample consisting of a single fluorescent microsphere. This allows direct determination of the point spread function for the optical instrument. Data collection in a sample is carried out by recording images of the sample with respect to the number of systematically varied changes in orientation and position of the structured-illumination pattern, as described below. Fourier transform of the acquired images produces the observable $\tilde{D}(k)$ that is a sum of the terms $\tilde{D}_m(k)=O_m(k)e^{i\Phi_{m0}}\tilde{S}(k-mp)$. Further analysis of the data, including determination of the pattern wave vector p and other parameters, leads to estimates of the intensities for the Fourier transform of the density distribution of fluorophores, $$\hat{\tilde{S}}(k) = \frac{\sum_{d,m} O_m^*(k+mp_d)\tilde{D}_{d,m}(k-mp_d)}{\sum_{d',m'} |O_{m'}(k+m'p_{d'})|^2 + w^2} A(k),$$

which can, by inverse Fourier transform, lead to a reconstructed distribution of fluorophores, or reconstructed image.

There are a number of deficiencies with regard to conventional 3D-SIM instruments, such as the conventional SIM instrument described with reference to FIG. 18. First, use of the diffraction grading to generate three coherent illumination beams is extremely inefficient, with only a few percent of the original laser-light intensity ending up in the three coherent illumination beams incident on the back focal plane of the objective. Second, the currently available 3D-SIM instruments require relatively lengthy adjustment periods in order to change the position and/or orientation of the structured-illumination pattern during data collection. These adjustment periods accumulate, over the operations undertaken to collect data from a particular sample, to produce relatively lengthy data-collection times for any particular sample. These lengthy data-collection times are not well suited for live-cell imaging and for imaging samples in which the spatial distribution and emission intensities of fluorophore emitters can change substantially data-collection time intervals. An additional deficiency is that the configuration and geometry of the currently available 3D-SIM instrumentation is particular for a narrow range of illumination wavelengths. To enable different-wavelength illumination sources to be used, complex and time-consuming instrument reconfiguration and re-adjustment is needed. Embodiments of the present invention address all three of the above-mentioned deficiencies as well as provide additional desirable features and characteristics.

Until recently, the readout speeds of suitable scientific cameras did not justify a significant effort to speed up 3D-SIM opto-mechanical processes. However, with the advent of scientific grade CMOS cameras featuring high quantum efficiency, low noise, and high pixel counts, slowly-shifting SIM patterns and long exposures can now be considered to be roadblocks that need to be circumvented or removed in order to achieve 3D-SIM instrumentation suitable for live-cell imaging.

Embodiments of the present invention efficiently use laser light to greatly increase the time efficiency for 3D-SIM data collection. Current 3D-SIM microscopes require relatively powerful lasers, greater than 100 mW, which are expensive, but which still entail long exposures to obtain adequate image signal to noise ratios. Indeed, the fraction of laser light reaching the back of the microscope objective in existing designs is only a few percent. Embodiments of the present invention increase efficiency of laser-light use by more than an order of magnitude higher and deliver high quality beam wavefronts which produce high contrast interference fringes. This is accomplished by replacing the inefficient, shifting and rotating grating with a system of beamsplitters and phase-shifting mirrors. The mirrors, attached to precision piezo actuators, move rapidly with fractional-wavelength displacements, settling in from a few milliseconds to less than a millisecond. The beam polarization geometry, employed in embodiments of the present invention, allows the use of dielectric mirrors, which generally exhibit more than 99 percent efficient.

As stated earlier, in 3D-SIM, three focused, phase coherent beams are introduced into the back focal plane of a high magnification, high numerical aperture (NA) objective. A 60×, 1.42 NA oil immersion objective would be typical. One beam is in the center of the back aperture and the other two are near the periphery. Maximum resolution is achieved for a given wavelength when the peripheral beams are separated by the maximum practical amount in the back aperture, producing the finest pitch fringe pattern possible for that wavelength. All three beams arrive at the sample as plane waves, with two wavefronts entering at high angles. Lateral offsets between adjacent fringe maxima are approximately 425 nm in the microscope sample plane.

Figure 19:
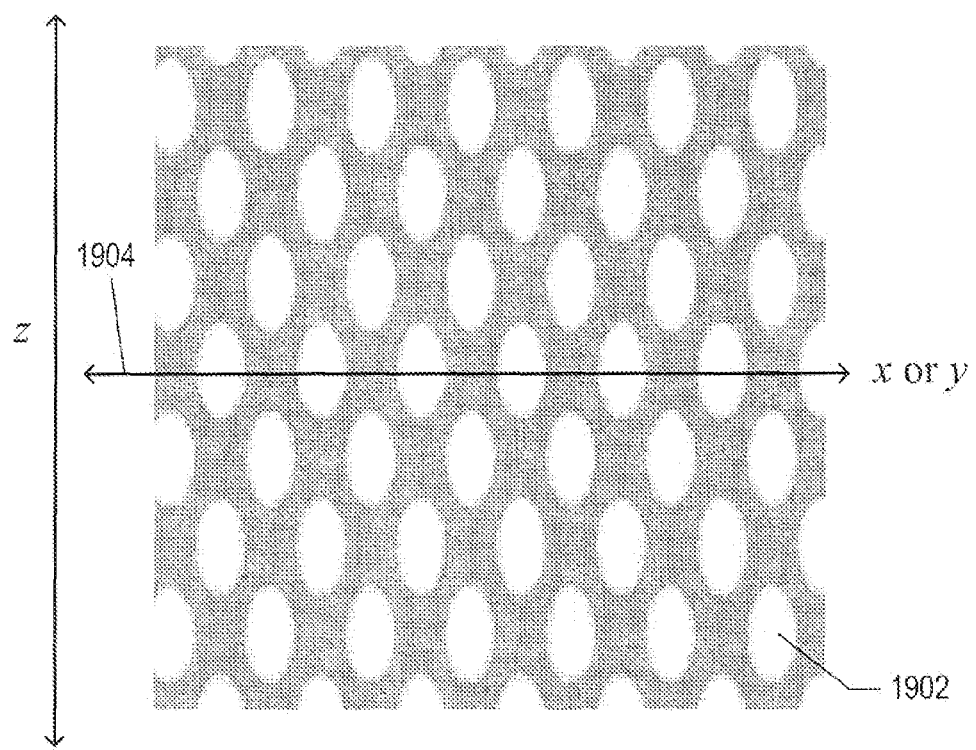
FIG. 19 shows a simulated cross-section of a typical 3D-SIM intensity pattern.

FIG. 19 shows a simulated cross-section of a typical 3D-SIM intensity pattern. The pattern features elliptical cylinders of high intensity light within a matrix of lower-intensity light. In FIG. 19, the elliptical cylinders are shown in cross-section, with each light-shaded ellipse, such as ellipse 1902, representing a cross section of an elliptical cylinder. When the intensity pattern, generated by interference of the three beams, is projected onto a sample plane, represented in FIG. 19 by horizontal line 1904, the interference pattern is seen, on the sample plane, as a set of parallel high-intensity lines spaced apart at a fixed distance.

The shape and size of the structured-illumination pattern is governed by the laser wavelength and the angle and amplitudes of the respective wavefronts. The location of the structured-illumination pattern with respect to the sample is, in embodiments of the present invention, determined by the phase relationships between the three illumination beams. The pattern can be displaced axially up and down by advancing and retarding the relative phase of central beam. A phase change of $\pi$ radians moves the pattern vertically by half a period. A $2\pi$ change reproduces the original pattern. Similarly, advancing and retarding the phase of the peripheral beams by equal and opposite amounts displaces the pattern laterally. In one embodiment of this invention, a single 3D-SIM pattern lateral displacement step is performed by displacing two mirrors by $\pm\lambda/10$, approximately $\pm 50$ nm, respectively.

At the sample, each of the three beams can be represented as a plane wave with a complex amplitude $E_m$, m=1,2,3.

$$E_m(x)=A_m\exp(-i(k_m x+\phi_m)),$$

where $A_m$ is the amplitude of beam m, and $k_m$ and x are the vector wave number and position in the sample plane, respectively, and $\phi_m$ is a phase under our direct control, with time-dependent factors, suppressed. A beam propagating in the direction of $k_m$ accumulates $2\pi$ radians of phase for each laser wavelength of displacement along that direction. E(x) is the (interfering) sum of the three field amplitudes at point x in the sample. The optical intensity, I, is proportional to the squared magnitude of the field:

$$I(x)=EE^*,$$

where * denotes the complex conjugate. In practice, properly aligned optics renders the effect of non-ideal, curved wavefronts in the sample plane to be negligible.

The laser beams are linearly polarized. Maximum fringe contrast, or fringe visibility, is obtained when the three beams are in a relative s-polarization state. S-polarization occurs when the electric field in each beam is perpendicular to the plane in which the three beams enter the back of the objective. This condition is created in the conventional-grating scheme by mixing the polarization state of the original laser beam, and then by passing it through a linear polarizer that co-rotates with the grating thereby losing half the light. Other SIM instruments employ active phase rotators, such as liquid crystal devices, but beam efficiency and wavefront quality and cost issues arise. Electro-optic and Faraday rotation devices raise these issues, as well, and are generally strongly wavelength-dependent. Embodiments of the present invention avoid the use of polarizers, because the linear polarization of the input illumination beam is maintained as the beam is split and directed through the SIM optical components, and has proper S-polarization at each optical interface at which non-S-polarized light would otherwise be absorbed.

Constructive and destructive interference occurs only when the beams are phase coherent with each other. This condition pertains rather naturally in a grating implementation. In embodiments of the present invention, with multiple beamsplitters, the optical paths of the three beams are controlled by the designer. The optical path lengths of the three beams are made equal to within the coherence length of the laser for each of the three angular orientations. Many solid state lasers suitable for fluorescence microscopy have coherence lengths of a few millimeters. Three-beam layouts on optical tables comprising beamsplitters and multiple mirrors with total path lengths exceeding one meter achieve excellent and stable fringe contrast with such lasers. A 3D-SIM microscope embodying the present invention is designed or adjusted to support beam path differences of a millimeter or less. Lasers with long coherence lengths are avoided to prevent parasitic interference between unavoidable reflections from beam path components.

Given that the phase shift mirrors used in the described SIM that represents one embodiment of the present invention move a few tens of nanometers, clearly thermal expansion, vibration, and other factors must be faced and dealt with. The optics must be enclosed in a compact thermally-stable and air-current free environment supported by a vibration-isolating floating table or the equivalent. Components that span the optical paths are machined from Invar. Measurements with an enclosed microscope prototype via interference fringe tracking have shown that thermally induced phase drift and residual air currents are negligible on a time scale of ten seconds (<2 degrees rms). Ordinary levels of sound and vibration in the room containing out test enclosure cause no disturbances, however, jumping on the floor causes a noticeable effect. Instrument vibration, which will tend to smear the contrast of the fringes, can be minimized by such steps as using liquid-cooled instead of fan-cooled cameras. Mechanical excitation of the instrument by the motion of the phase mirrors, if present, is small.

Typically, 3D image stack acquisition is expected to take one second or less, and so effectively instantaneous thermal stability is achieved. However, environmental changes taking place over minutes and hours will alter the phase relationship of the three beams, thus displacing the interference pattern at the sample plane laterally and in z. A method is incorporated into the disclosed SIM to measure the phase relationship of the three beams by picking off beams samples between the beam align/focus ("BAF") lens and objective, and collimating and crossing the beams via a lens onto the face of a CCD or other pixilated optical detector. Ideally, three interferograms comprising different overlapping beam combinations are captured simultaneously, e.g., Center-Left, Center-Right, and all three. Beam pairs are selected by blocking the unneeded beam with a mask in a focal plane. These are acquired for each beam triplet in all three arms of the instrument. The phase computed from the data would be used to optically close the feedback loop via corrections issued to the phase mirrors: Well-executed, with temperature-stable CCDs, such a scheme obviates the need for in situ position feedback mechanisms for the phase mirrors, such as expensive capacitance sensors.

Explicit control over the relative phases of the three beams provides another significant advantage over grating-based and some other 3D SIM architectures. Lateral displacement of the grating advances and retards the phases of the outer beams respectively, but does not affect the zero-order (center) beam passing through the grating. Thus the depth (in z) of the 3D interference pattern at the sample is fixed for a grating which has a fixed-z location in the optical train. The depth of the 3D pattern must be tuned. The relation of the pattern to the sample plane is studied by acquiring 3D SIM image stacks of a single sub-diffraction (e.g., 100 nm) fluorescent bead and measuring the modulation depth at the main fringe spatial frequency but also at the higher spatial frequency, which derives from the angles of the two outer beams. With a grating-based system, measurements are made, and then the grating assembly is moved forward or backward in z with respect to a collimating lens by a small amount, order 100 micrometers, and the measurements are repeated. The process is iterated until an optimal result is achieved. The grating position adjustment is a tedious, manual task, for one wavelength in one orientation only. It is thus extremely unlikely that the pattern depth is optimized in B for all wavelengths, or, for a grating system lacking perfect three-fold symmetry, for all angles. The easy control over the relative phases of the three beams in SIMs of the present invention permits the modulation-depth mirror-phase parameter space to be mapped rapidly and automatically for each wavelength and orientation. Setting the phase mirrors to their optimal modulation location, the phases captured by the phase-feedback system are then recorded into a mirror phase look-up table. Given the tight opto-mechanical coupling and proximity of the phase feedback system to the objective, and a judicious choice of materials, the mirror phase table remains accurate over a reasonable temperature range, say a few degrees C.

Figure 20A:
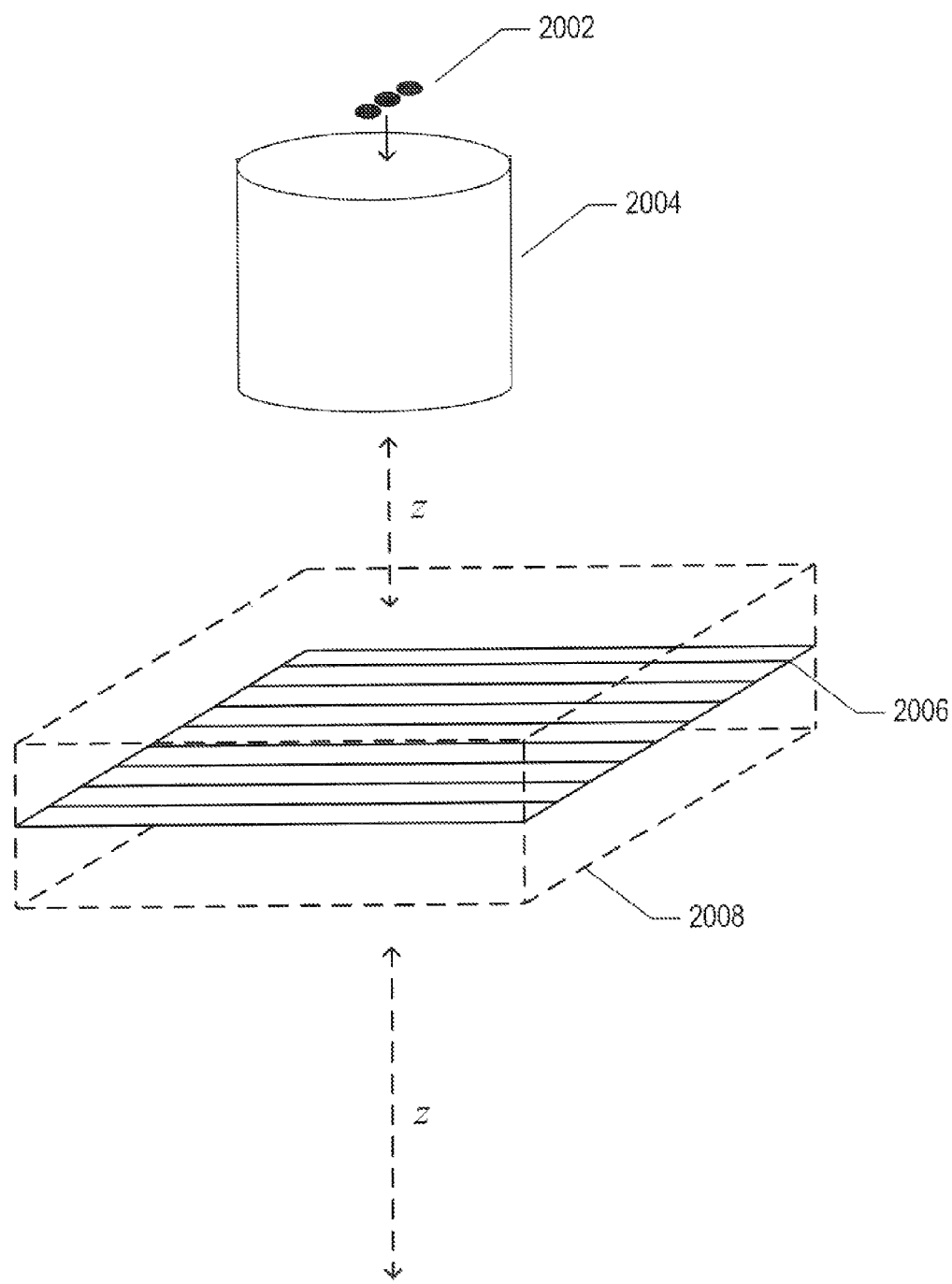
FIGS. 20A-I illustrate data collection for 3D-SIM imaging of a sample plane, as discussed above.
Figure 20B:
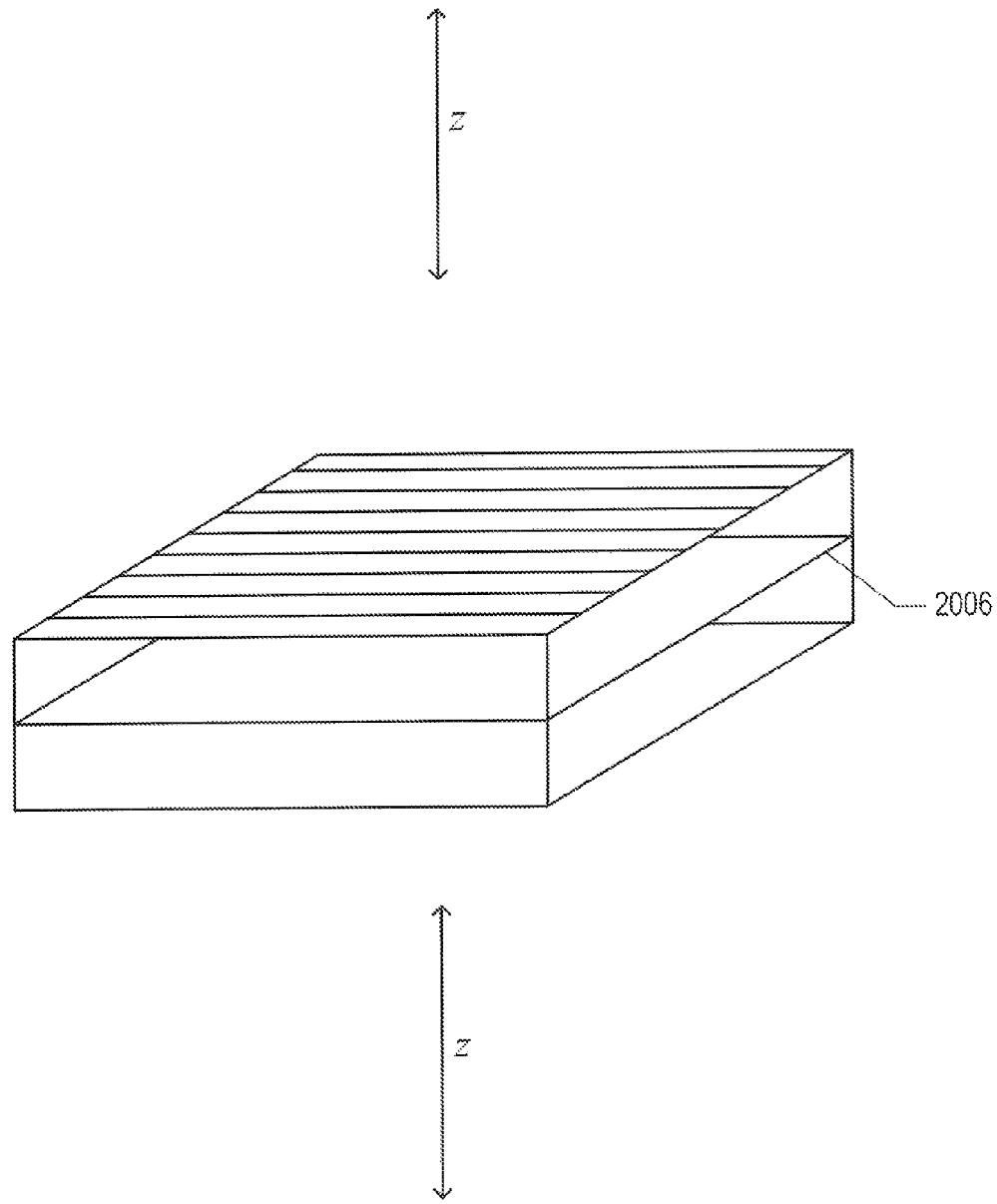
Figure 20C:
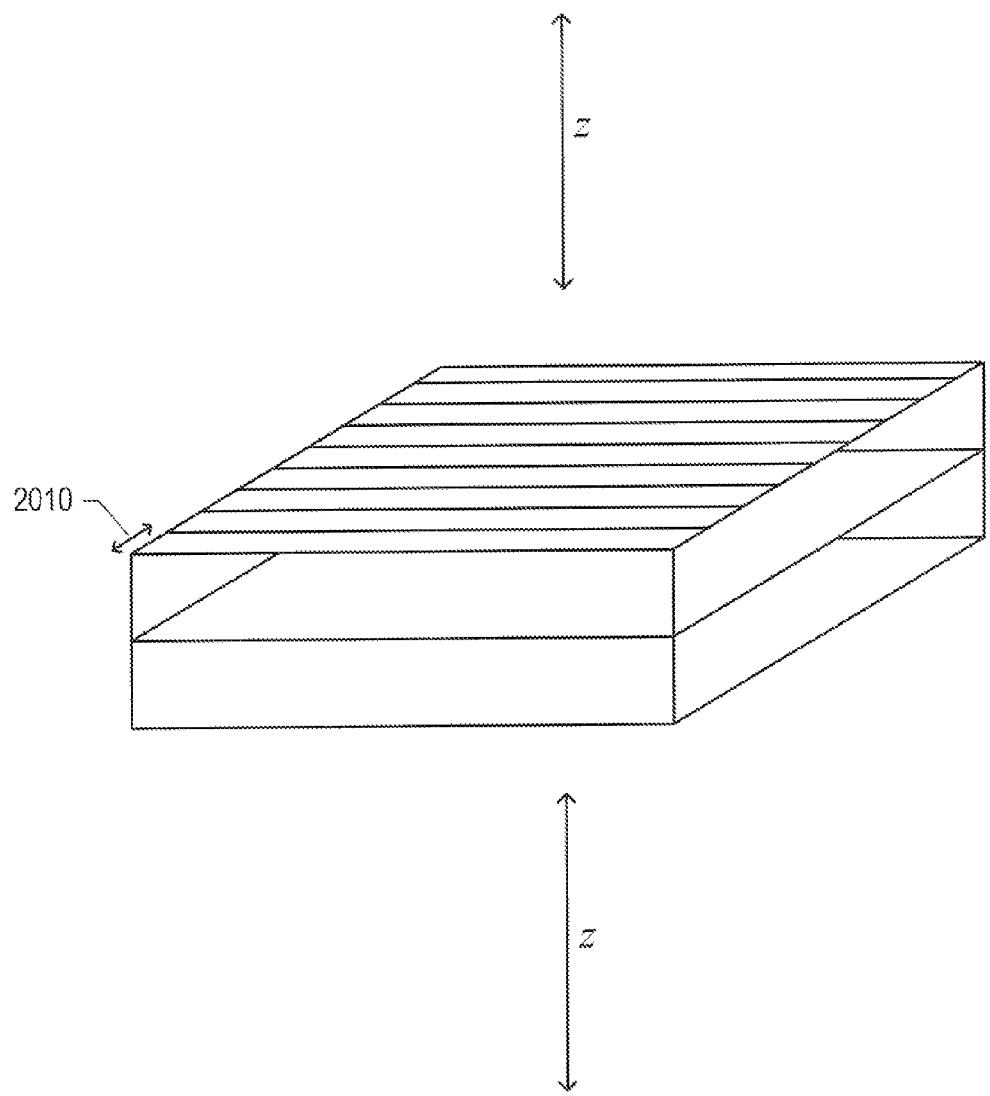
Figure 20D:
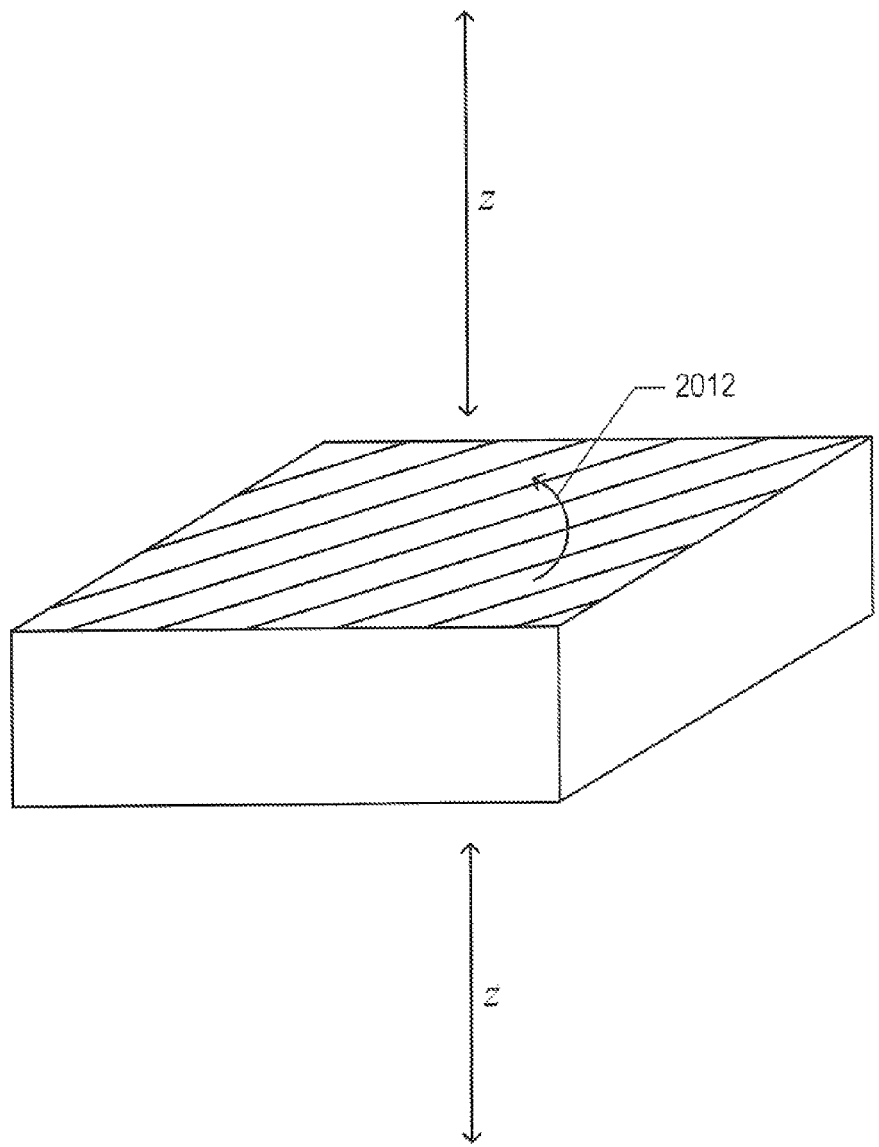
Figure 20E:
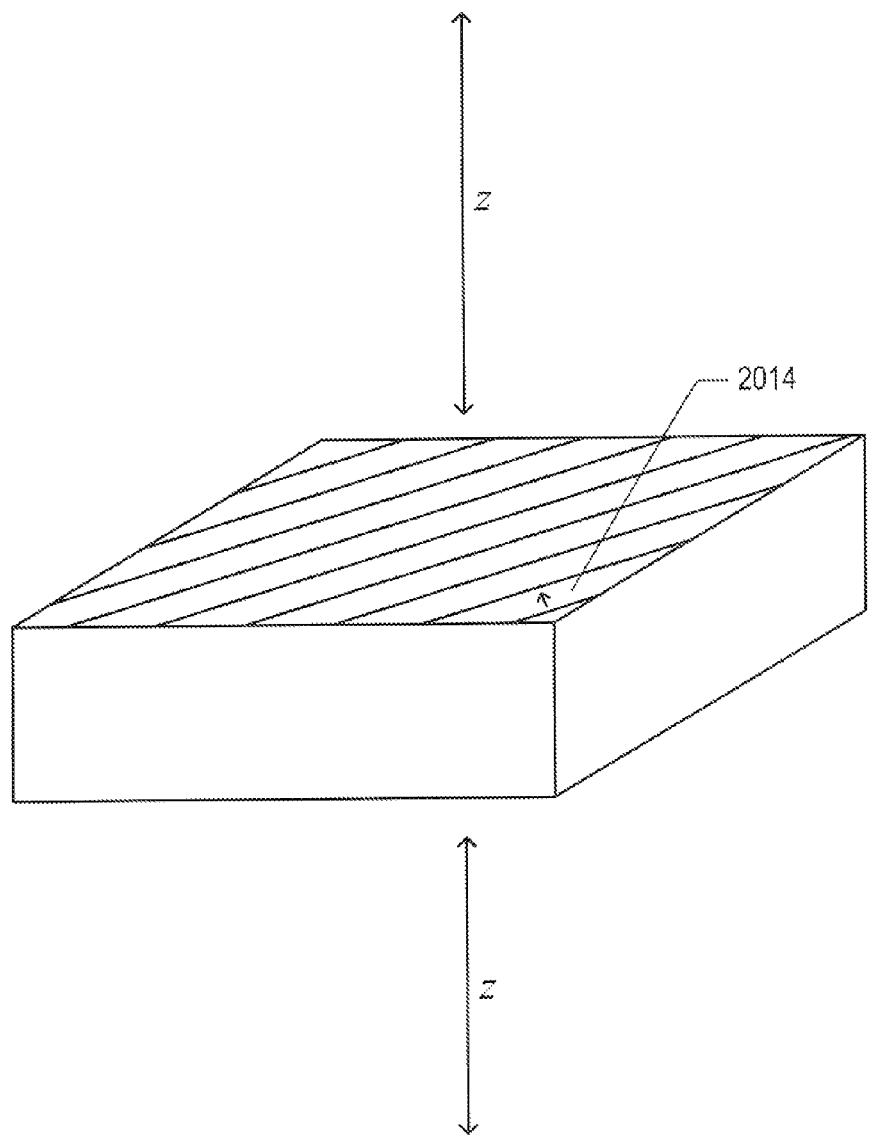
Figure 20F:
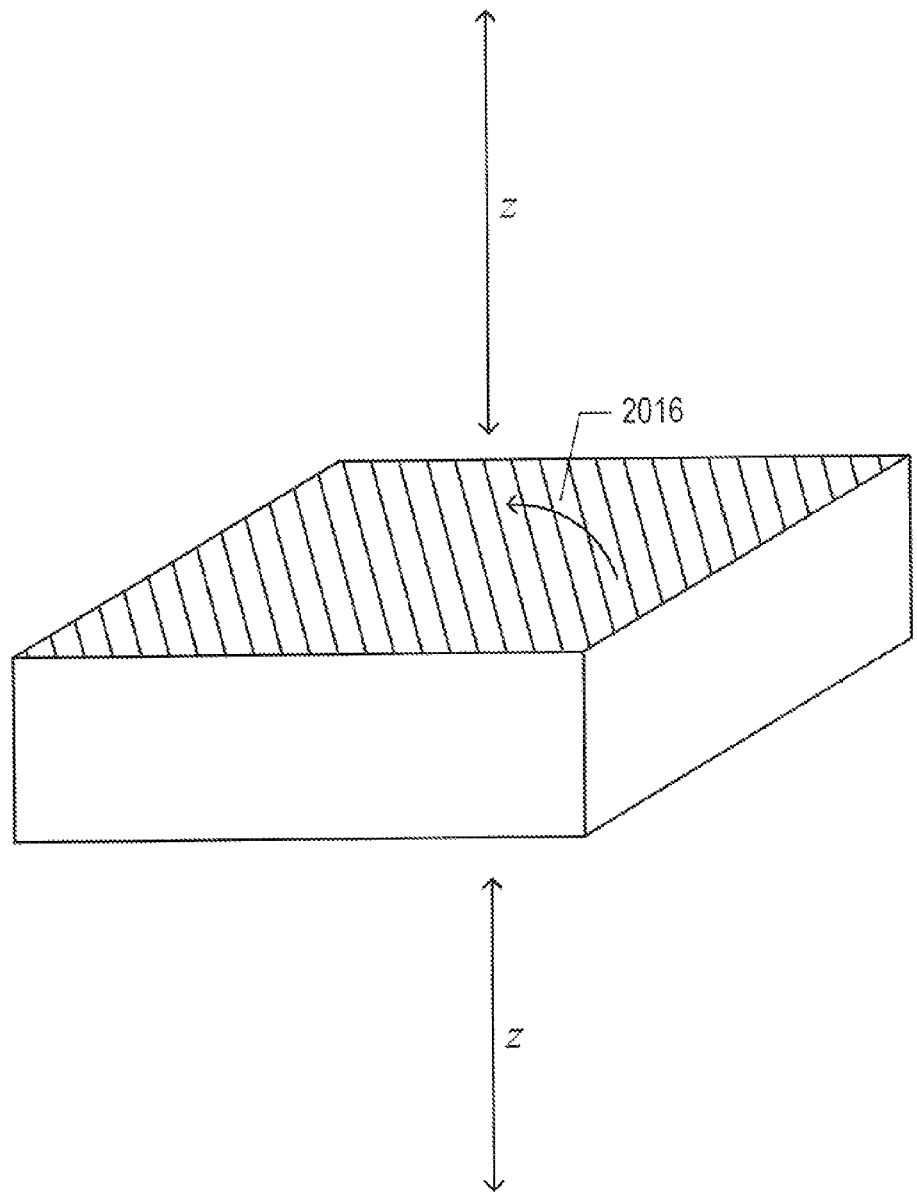
Figure 20G:
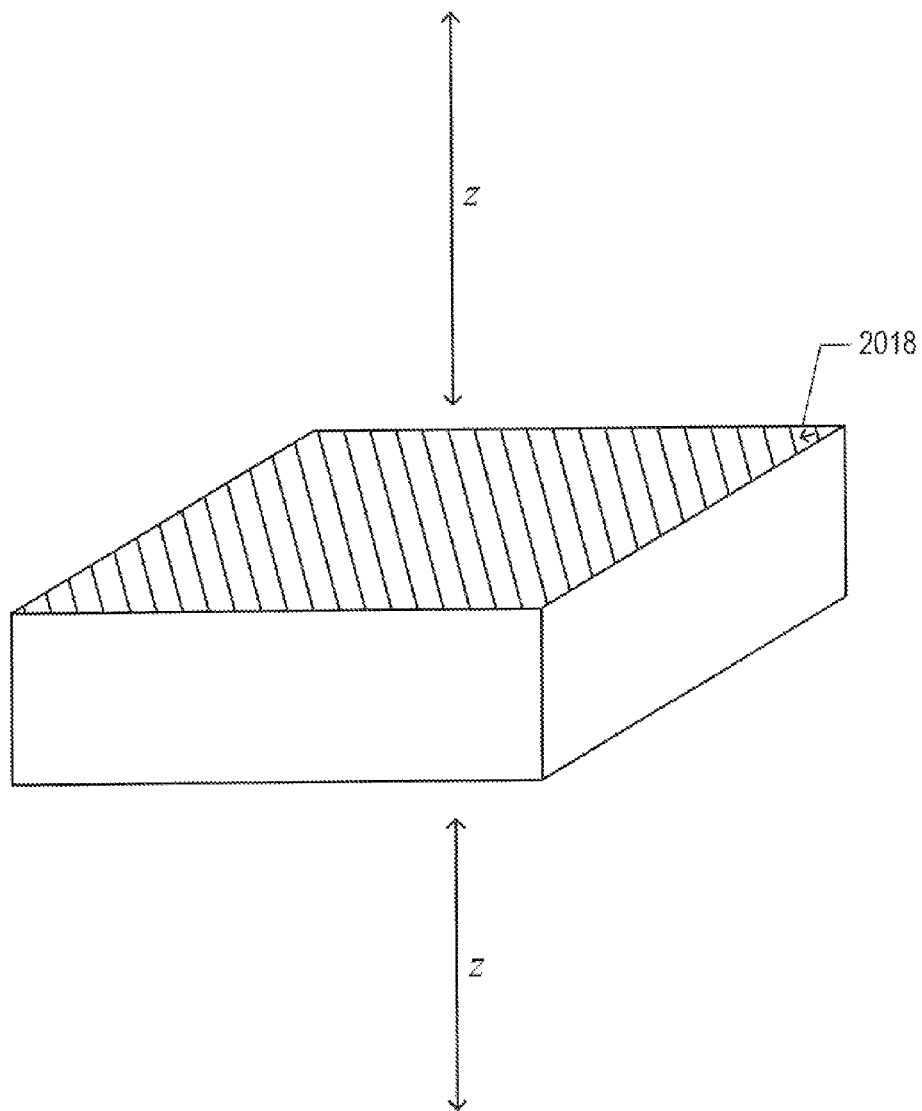
Figure 20H:
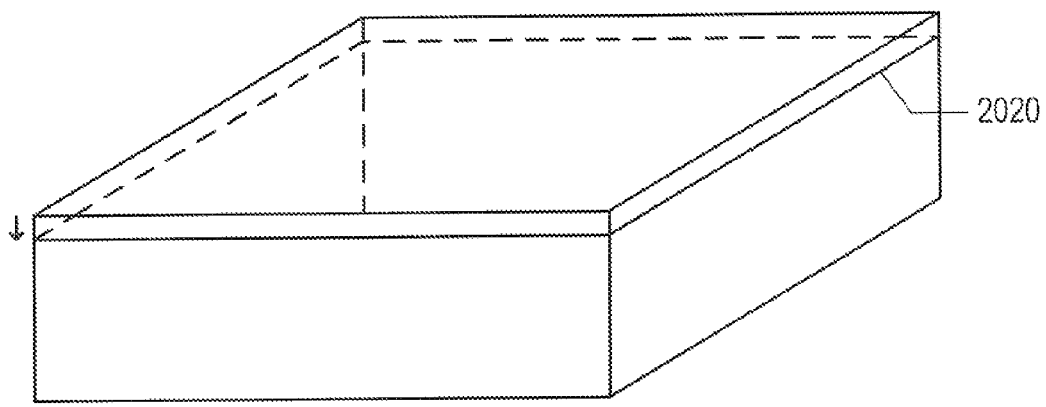
Figure 20I:
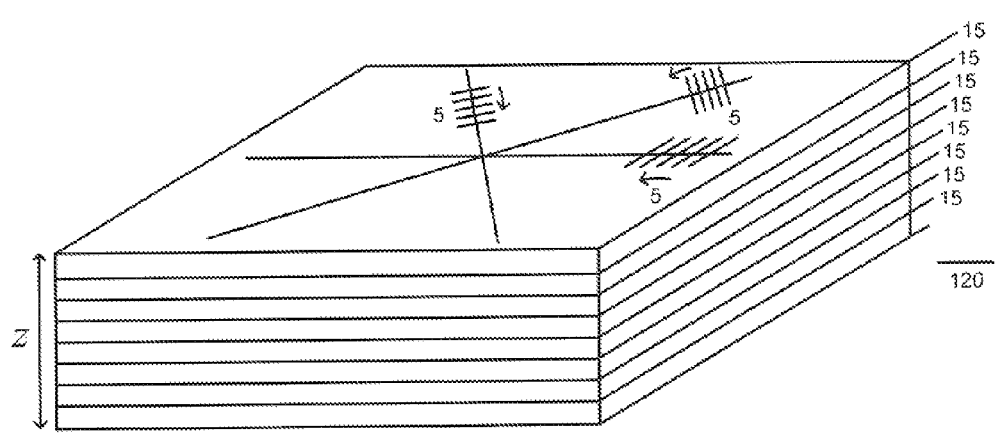

FIGS. 20A-I illustrate data collection for 3D-SIM imaging of a sample plane, as discussed above. FIG. 20A shows the geometry of the imaging technique. As discussed above, an interference pattern 2002 is focused at the focal plane behind the objective lens 2004 causing the interference pattern to be projected through the objective and focused on the plane of the sample 2006 to be imaged. As discussed above, in order to reconstruct a higher-resolution image for the sample plane 2006, the mathematical technique for 3D-SIM data processing reconstructs the higher-resolution image for the sample plane from data collected from a sample volume, shown by the dashed lines 2008 in FIG. 20A, that includes the sample plane and volumes both above and below the sample plane. First, as shown in FIG. 20B, the interference pattern is focused onto the top of the sample volume (2008 in FIG. 20A). A first image is recorded with the interference pattern positioned as shown in FIG. 20B. Then, as shown in FIG. 20C, the interference pattern is shifted, in a direction orthogonal to the lines of the interference pattern 2010, and a second image collected. In one embodiment of the present invention, five lateral shifts, such as that shown in FIG. 20C, are carried out to produce five different, laterally shifted interference patterns from which five images are collected. In other words, the spacing between interference-pattern lines is divided by six to generate a finer spacing distance, with five shifts needed to sample the finer-spacing distance. Then, as shown in FIG. 20D, the interference pattern is rotated 2012 by 60 degrees and a next image recorded. As shown in FIG. 20E, the interference pattern is then laterally shifted 2014 in a direction perpendicular to the lines of the interference pattern and another image is recorded. As with the first orientation of the interference pattern, shown in FIG. 20B, five different shifts are carried out in the second orientation. Then, as shown in FIG. 20F, the interference pattern is shifted again by 60 degrees, and a next image is recorded. As shown in FIG. 20G, the interference pattern is laterally shifted 2018 from the position shown in FIG. 20F and another image recorded. As with the first two above-discussed orientations, five lateral shifts are carried out in the third orientation shown in FIGS. 20F and G. Once 15 images. five images in each of three orientations, are recorded from the first plane, the interference pattern is then focused on a second plane 2020 in FIG. 20H, and 15 images are recorded in this second plane in the same fashion as 15 images were collected from the first plane, as shown in FIGS. 20B-G. A total of eight planes regularly spaced through the sample volume in the z direction are sampled. Thus, as shown in FIG. 20I, the volume enclosing the sample plane generates 120 different recorded images, 15 images per plane in the z direction generated from three different orientations of the interference pattern in each plane.

Figure 21:
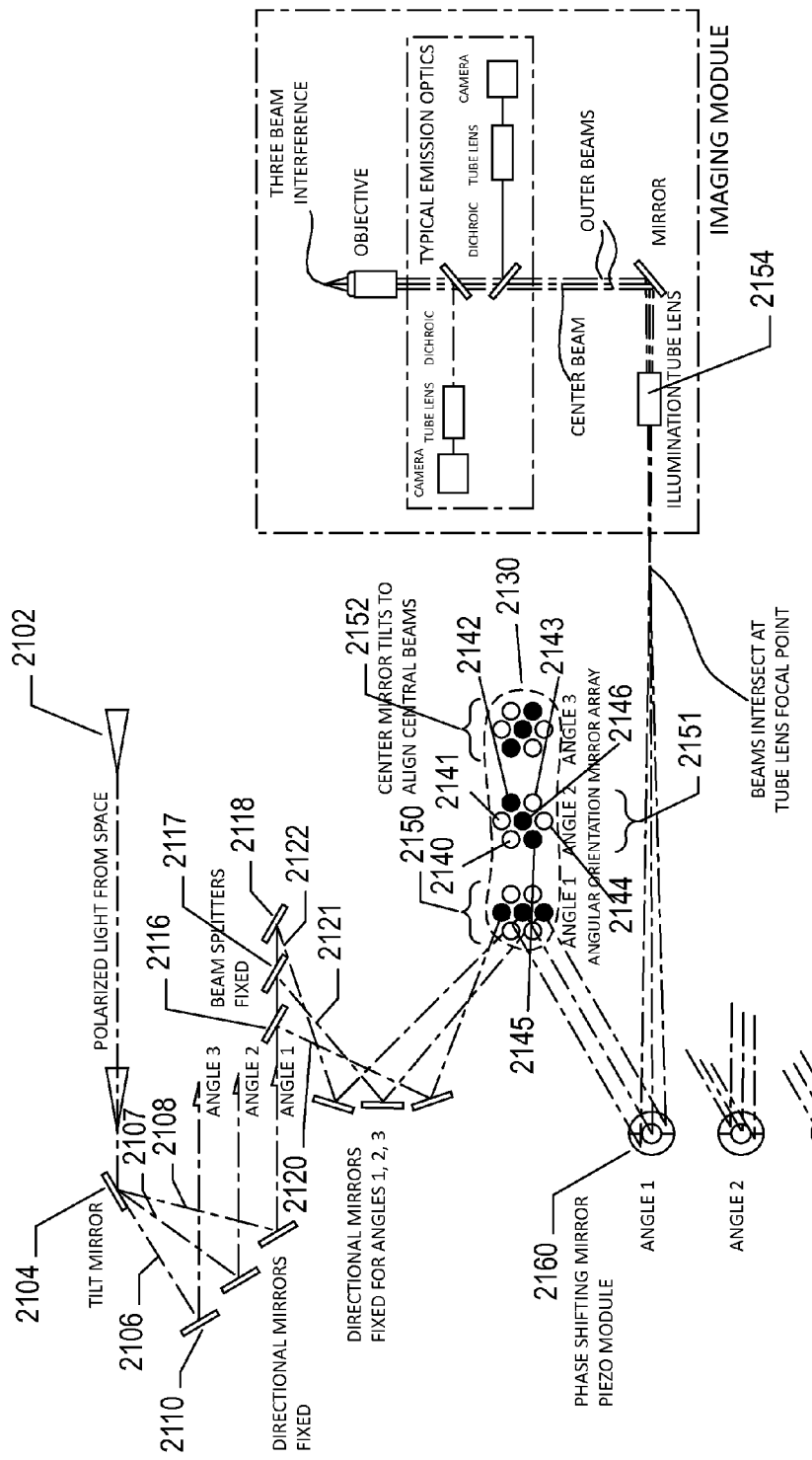
FIG. 21 provides a schematic that illustrates many features of one embodiment of the present invention.

FIG. 21 provides a schematic that illustrates many features of one embodiment of the present invention. An expanded, collimated laser beam 2102 enters at the top of the diagram. In general, beams from multiple lasers may be combined with dichroic elements for capturing images in different wavelengths. The production of high contrast interference fringes necessitates the use of high quality optical components and careful metrology. The laser employed in one embodiment of the present invention is a Sapphire-488 (20 mW) made by Coherent. The light is launched into a polarization-maintaining single mode fiber with collimating lenses on either end. The "Kineflex" system manufactured by Qioptiq (formerly Point Source) is used in this embodiment of the present invention, which additionally expands the beam using a dual-mirror 4× reflective beam expander (Thorlabs).

A fast tilt mirror 2104 directs the beam to one of three optical trains 2106-2108. This mirror need not be as fast as the phase shifters. Fused silica dielectric mirrors employed were $\lambda/10$ flatness, 5-10 scratch-dig (Thorlabs). In each of the three trains, the beam is directed, by directional mirrors such as directional mirror 2110, into a set of beam splitters 2116-2121. The fast tilt mirror essentially selects one of three structured-illumination-pattern orientations, each orientation representing a rotation of 120° with respect to each of the other two orientations.

The three beams 2120-2122, a "triplet," are directed via mirrors to a common beam aligner module 2130. The relative intensities of the three beams may be optimized for maximum 3D-SIM reconstruction efficacy by careful design of the beam splitter ratios at the laser wavelengths of interest. The beam aligner module comprises seven small mirrors, six 2140-2145 in a circle, and one 2146 at the center. The six outer mirrors are adjusted and then fixed. A given triplet lies in a plane, and reflects from the center mirror and two outer mirrors. The triplets can be generated in three different orientations, depicted schematically as Angle 1, Angle 2, and Angle 3, 2150-2152, respectively. The outer two mirrors are aimed so that the three beams comprising a triplet overlap at the back aperture of the BAF lens 2154. The outer mirrors are separated to each subtend an angle, $\theta$, of approximately 20 mR. The center mirror aims to direct the center beam straight down the optical axis. Because the center beam from each triplet must arrive at the center mirror from a different angle, the center mirror needs to be a fast tilt mirror, adjusted once for each triplet. Alternatively, a single tilt mirror may be used to accomplish the initial aiming and triplet-aiming tasks simultaneously.

The phase-shifting module 2160 comprises three small mirrors affixed to three independent piezo displacement modules. This module introduces relative phase shifts among the beam triplet to change the position of the structured-illumination pattern. The pattern can be shifted laterally, in the x and y directions, and vertically, in the z direction, where the directions x, y, and z are instrument-frame directions. A commercially available closed-loop piezo actuator has a stroke of 2 μm, a resolution of 0.03 nm, and a natural resonance frequency of 25 kHz. The mirrors are shaped such that one mirror controls the central beam phase, and the other mirrors control the phases of the outer beams for each triplet, as depicted schematically. The three mirrors need not lie in a plane, as long as total beam path lengths are respected. The angle of incidence on the mirrors is not normal (perpendicular), to avoid reflecting back to the beam aligner module. It is kept near-perpendicular, however, to avoid coupled beam translations, and to permit the use of efficient dielectric mirrors, which tend to induce undesirable elliptical polarization in beams that are a mixture of s and p polarization. If preferred, piezo control of only the two outer mirrors can be sufficient to control the relative phases of the three beams. The three beams of a triplet overlap at the back aperture of the BAF lens of focal length $f$. The three beams come to a focus at distance $f$, with the outer focal spots displaced by a distance $d=f\theta$. For a BAF lens with $f=180$ mm, and for $\theta=20$ mR, the displacements d=3.6 mm. The separation of the outer mirrors is engineered such that the displacement d is optimized for the selected microscope objective. The choice of the BAF lens focal length is determined by the beam diameter, the required illumination spot size at the sample, and mechanical design considerations for the mirror mounts. The three beams enter the objective 2170 and create the 3D-SIM pattern. Unlike the grating-based schemes, the system is highly achromatic, with the outer beam positions naturally optimized for each wavelength.

Figure 22:
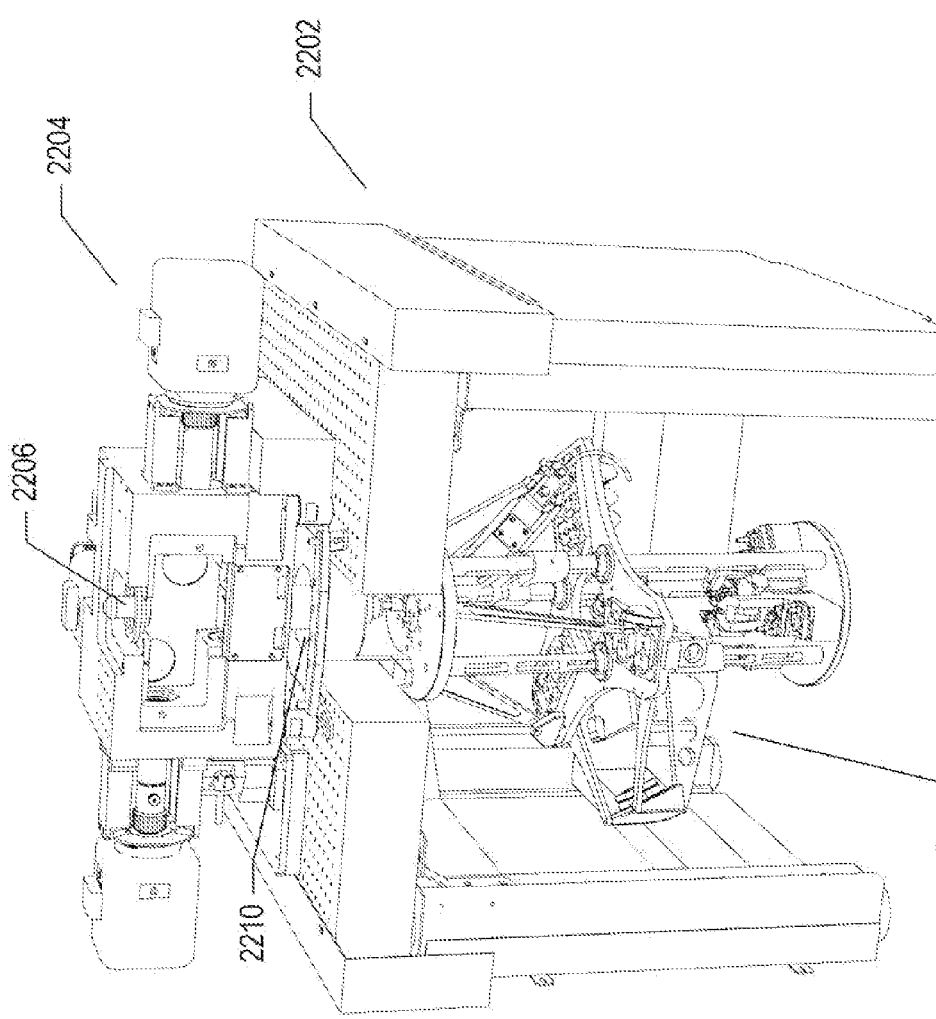
FIGS. 22-29 further illustrate one embodiment of the present invention.

FIGS. 22-29 further illustrate one embodiment of the present invention. These figures provide mechanical illustrations of the SIM that represents one embodiment of the present invention. FIG. 22 illustrates the SIM within the context of the optical bench of a 3D-SIM fluorescence microscope. The optical bench 2202 supports a central optics stage 2204 that includes the wide-angle objective 2206. The SIM that represents one embodiment of the present invention 2208 is mounted below the optical bench to direct the three incident beams that produce the structured-illumination pattern upward vertically through aperture 2210 to the back of the focal plane of the objective lens.

Figure 23:
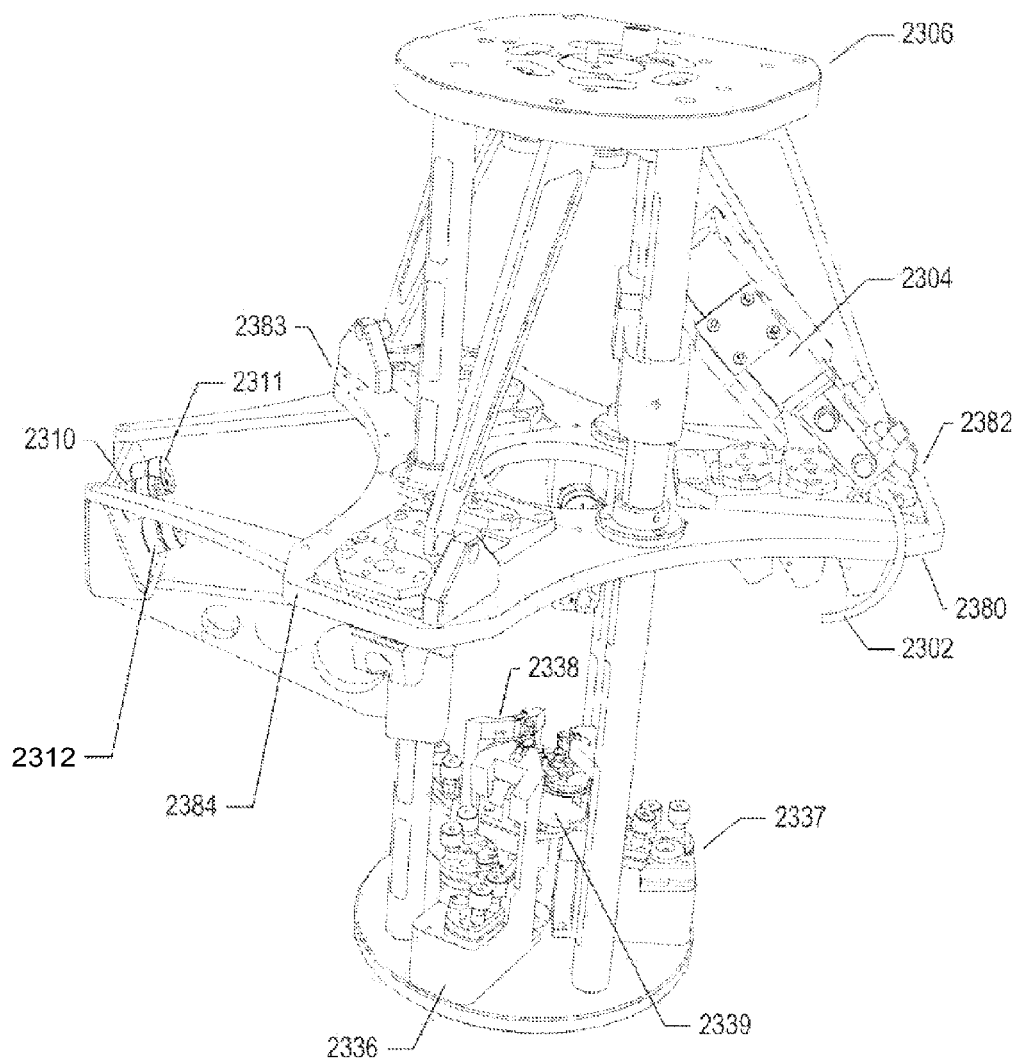
Figure 24:
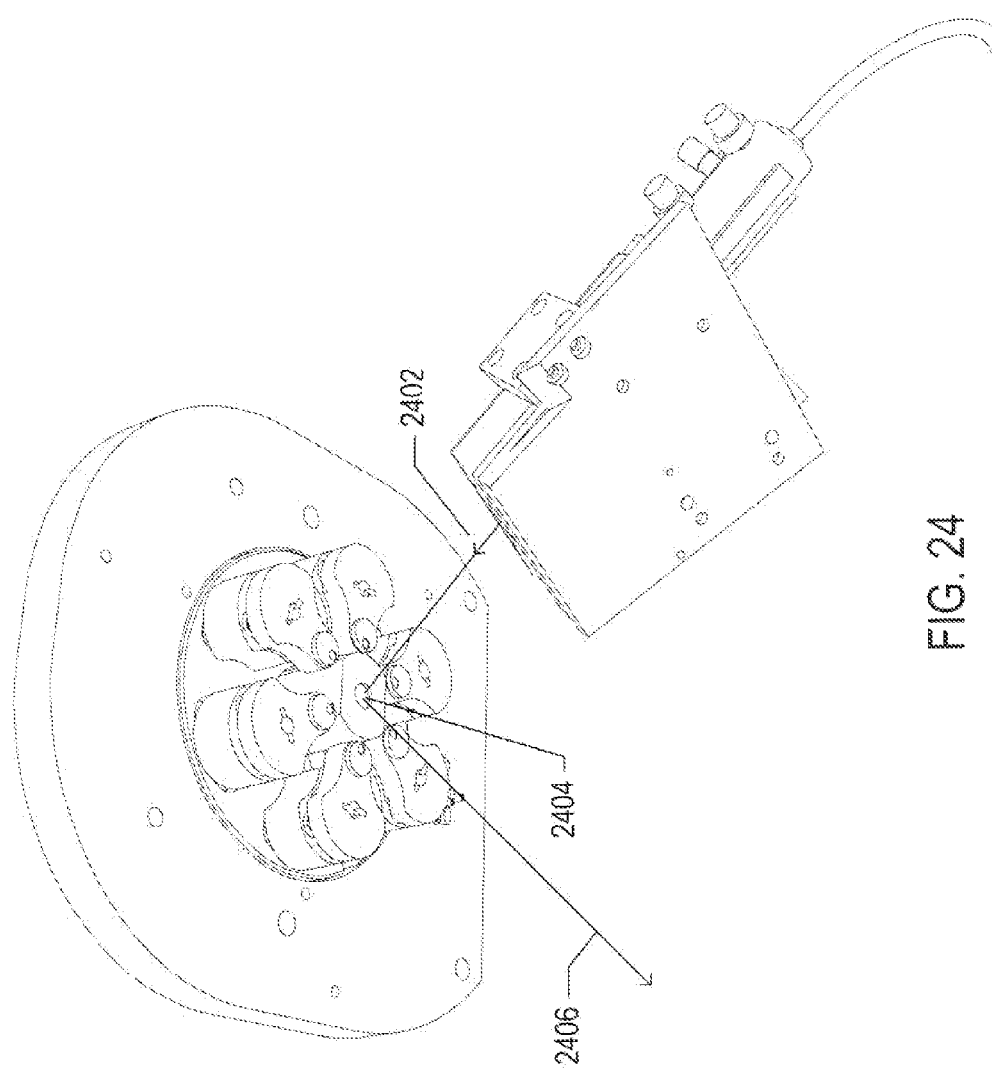

FIG. 23 illustrates the SIM. The polarized laser light is received via a phase-maintaining optical cable 2302 that is input to the beam expander 2304. A tilt mirror (2104 in FIG. 21) is located underneath a vertical plate 2306 at the top of the SIM. The tilt mirror serves as the central mirror (2146 in FIG. 21) of the beam aligner module, also located below plate 2306. FIG. 24 illustrates the expanded, polarized light 2402 (2102 in FIG. 21), impinging on the tilt mirror 2404 (2104 in FIG. 21) and being reflected towards one of three different directional mirror 2406 (2106 in FIG. 21). The tilt mirror 2404 essentially selects one of three directional mirrors (2310-2312 in FIG. 23) to which to direct the incident polarized, expanded input beam. Each of the three directional mirrors represents the starting point for a light path that provides one of three different rotational orientations of the structured illumination pattern, each orientation rotated 120° with respect to the other two orientations.

Note that the central horizontal plate (2380 in FIG. 23) includes three arms 2382-2384 with axes that are orientated with one another at angles of 120 degrees. Thus, the directional mirrors (2310-2312 in FIG. 23) each directs light to a different one of these three arms, to each of which a series of beamsplitters (2116-2118 in FIG. 21) are attached.

Figure 25:
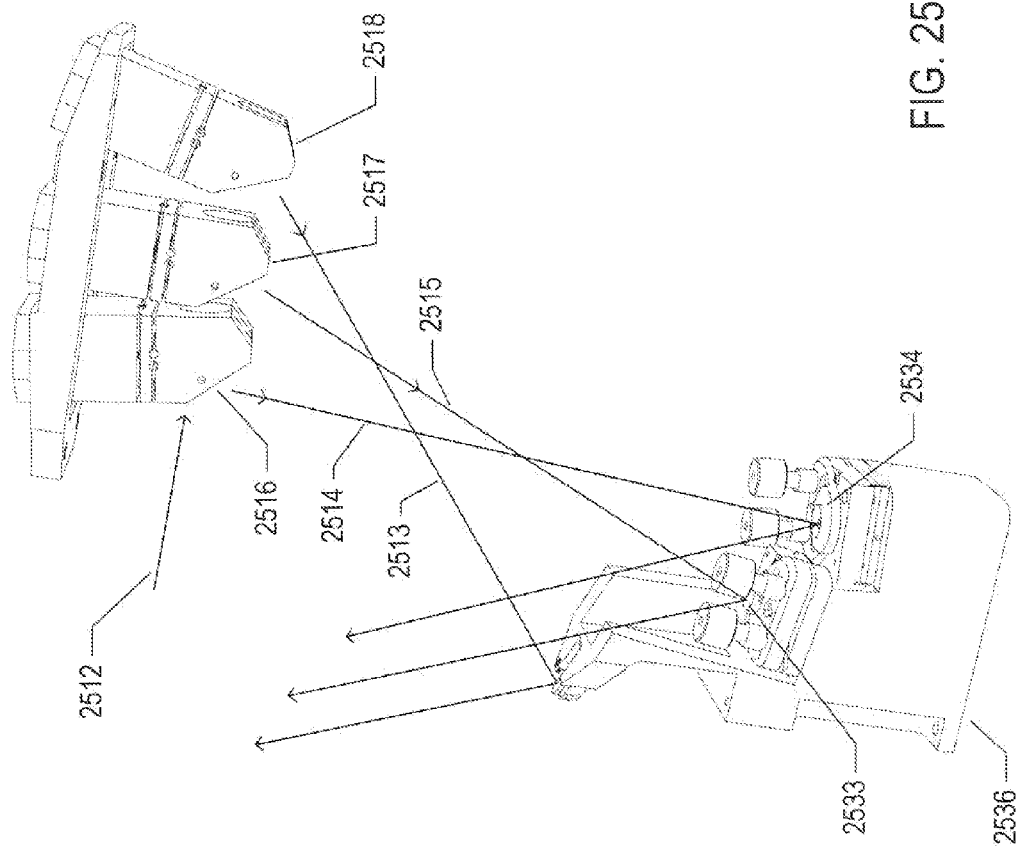
Figure 26:
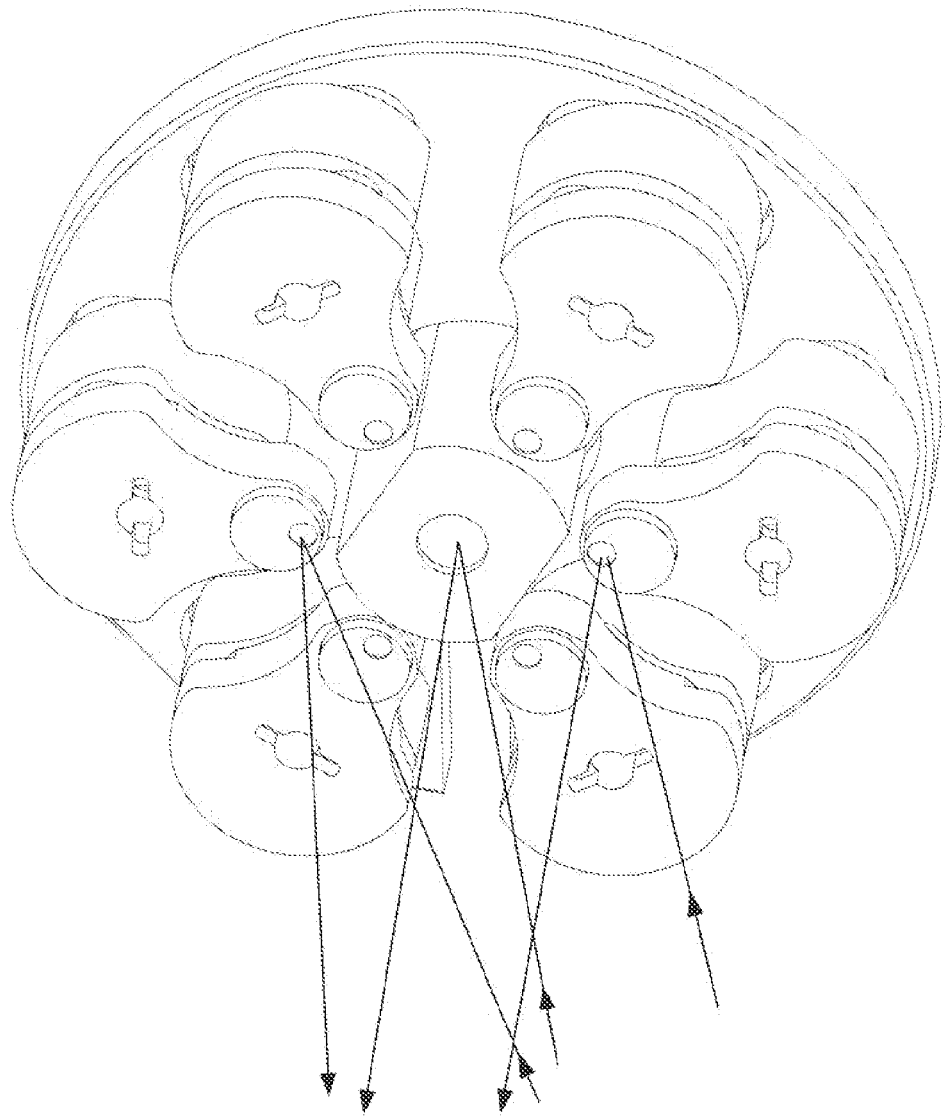
Figure 27:
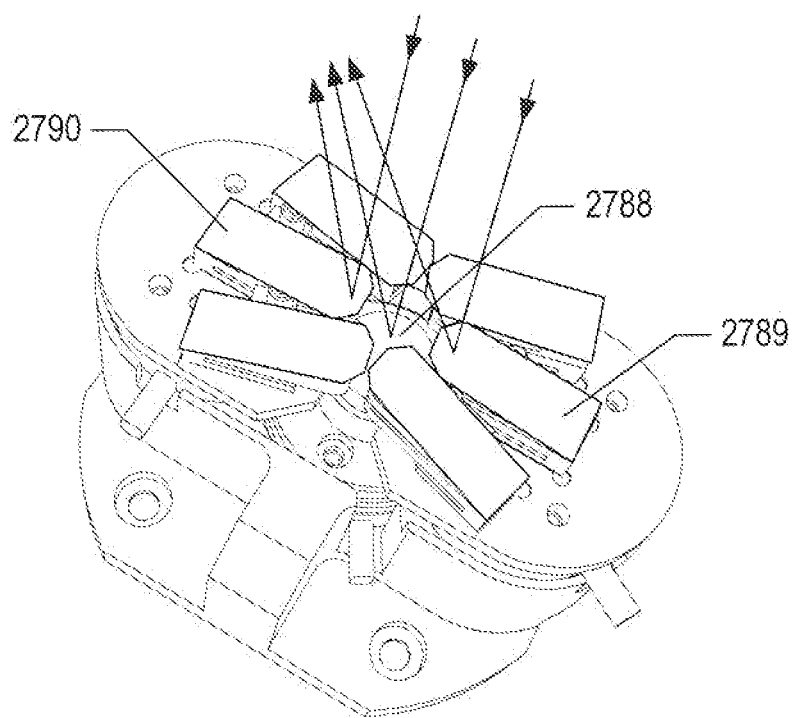
Figure 28:
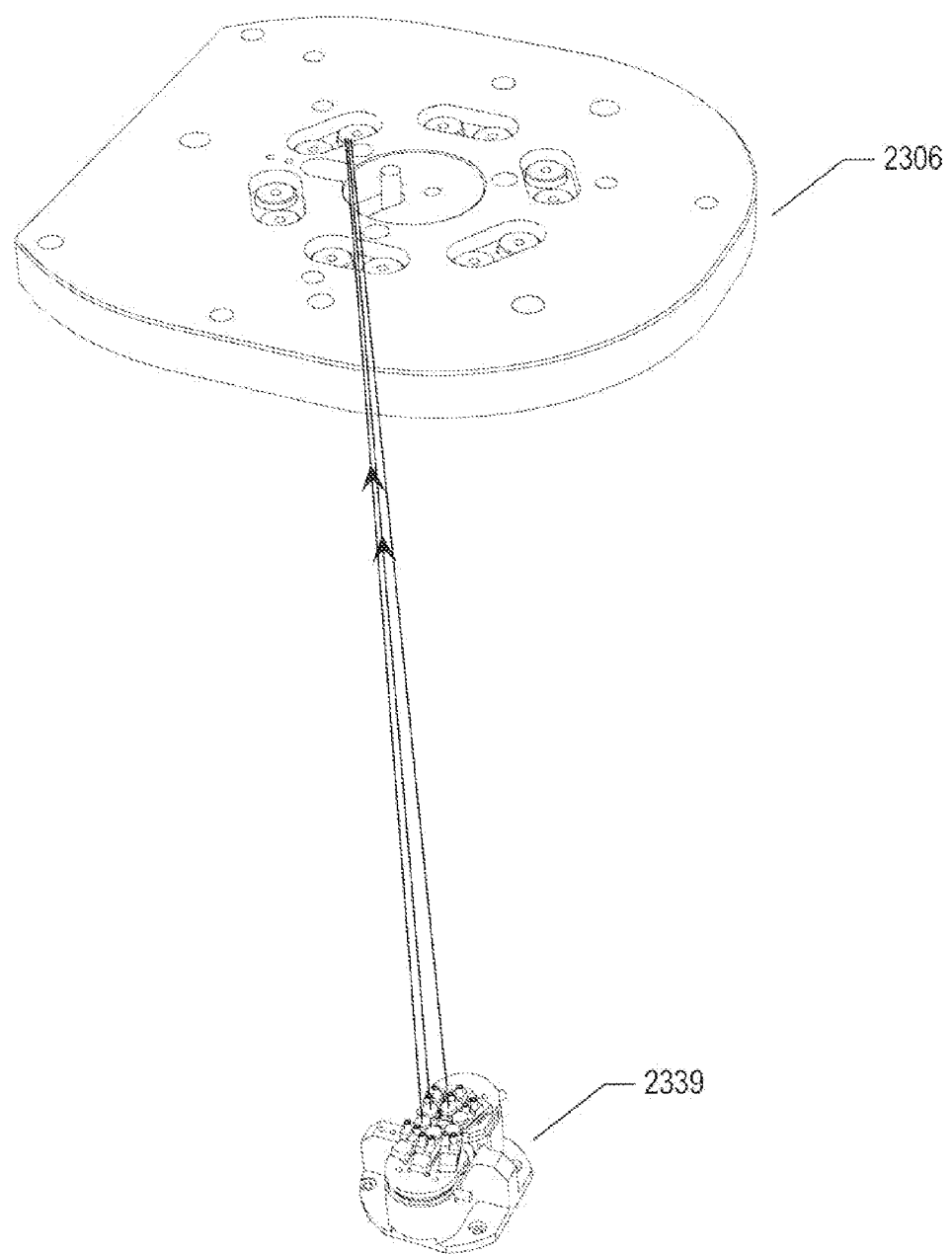
Figure 29:
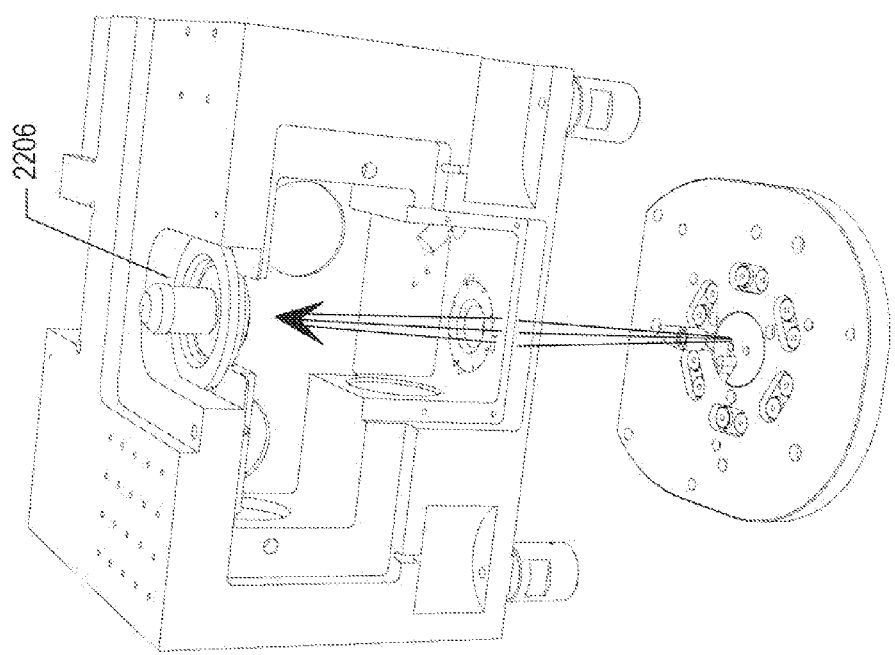

FIG. 25 shows splitting of a polarized, expanded beam by three beam splitters associated with one arm of the central horizontal plate of the stem. The three beam splitters 2516-2518 split the incident beam 2512 to form a triplet of three coherent beams 2513-2515 that are directed to three corresponding directional mirrors 2532-2534 that direct the three coherent beams upward to the beam aligner module bounded below the top horizontal plate (2306 in FIG. 23) of the SIM. Three different directional-mirror assemblies, such as directional-mirror assembly 2536 in FIG. 25, can be seen at the base of the SIM in FIG. 23, 2336-2338. FIG. 26 shows the beam triplet reflected from the directional mirrors 2532-2534 in FIG. 25 impinging on, and reflected from, the beam aligner module towards the phase-shifting module (2160 in FIG. 21). A phase-shifting module can be seen mounted at the base of the SIM 2339 in FIG. 23. FIG. 27 illustrates the phase-shifting module in greater detail. For each different orientation, a triplet impinges on a central mirror 2788 and onto side mirrors 2789 and 2790. As discussed above, the phase-shifting mirrors introduce relative phase shifts between the incident beams of the triplet beam in order to change the position of the structured-illumination pattern with respect to an instrument reference frame. Finally, as shown in FIG. 28, the phase-shifted beam triplet is reflected from the phase-shift module 2339 through an aperture in the top horizontal plate 2306 of the SIM and, as shown in FIG. 29, directed, at proper orientation and separation, to the back focal plane of the objective 2206.

FIG. 30 shows an updating MatLab display used in tuning a 3D-SIM according to one embodiment of the present invention. The pitch and orientation of the 3D interference pattern at the sample is tuned by altering the angle of the outer beams with respect to the center beam, which is well-centered on the optical axis. Fluorescence targets are subject to photobleaching, and yield rather low SNRs for this purpose, so the beams are aligned by measuring an interference pattern at a beam crossover, which is conjugate to the image plane. A camera image plane may be placed at the crossover before the BAF lens, or the phase feedback system may be used if it is in operation. A tiny FireWire-800 camera with 1280×960 3.75 µm pixels was used at the crossover (Flea 2, Point Grey Research Inc.). The top panel 3002 of the MatLab display is the (offset) data overlaying the fits for three rows separated by 10 pixels. The middle panel 3004 displays the phase offsets for the three rows and the bottom displays the inferred fringe angle with respect to the camera horizontal and the fringe pitch. To begin, the left beam is blocked and the right beam is set to a satisfactory angle with respect to the center beam; the angle and pitch of the interference pattern are recorded. The beam blocker is swapped, and then the left beam is carefully tuned, adjusting multiple mirrors, to match the recorded values. The mirrors can be aimed in pitch and yaw by turning 100 TPI screws in custom mirror fixtures which are either flexure-mounted or kinematically-mounted with springs. The process is repeated for the other arms. Rather good pitch agreement between the three arms can be obtained. If the left-center- and center-right pitches on a given arm are not commensurate, the result is a tilt of the interference plane with respect to the sample plane. Mirror-tuning precision is such that this can be rendered negligible. If the angles are not commensurate, this can complicate the 3D interference pattern. The beam is aimed such that angle-mismatch subtends a small fraction of a fringe pitch across the whole field of view.

Although the present invention has been described in terms of particular embodiments, it is not intended that the invention be limited to these embodiments. Modifications will be apparent to those skilled in the art. For example, a variety of alternative embodiments of the SIM can be designed and constructed to provide the functionality of the SIM illustrated in paragraphs 21-29. For example, in the embodiment of the SIM shown in FIGS. 21-29, the tilt mirror, (2104 in FIG. 21) is also used as the central mirror of the beam aligner module (2150 in FIG. 21). In alternative embodiments, a separate tilt mirror may be employed for tilt mirror 2104. Many different electro-optical-mechanical components from many different vendors can be used for the various components shown in FIGS. 21-29. The dimensions, geometry, and configuration of the SIM may be modified to accommodate alternative types of optical components and alternative light-paths and light-path geometries. A variety of additional calibration and control components and functionality may be employed, in a 3D-SIM fluorescence microscope, in order to calibrate and control operation of the SIM, including software components that execute on a computer system coupled to the 3D-SIM fluorescence microscope. The calibration and control systems and functionality can be implemented by using many different physical and computer-software components.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purpose of illustration and description. They are not intended to be exhaustive or to limit the invention to the precise forms disclosed. Many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents:

What is claimed is:

1. A structured-illumination module included in a 3D-structured-illumination-based fluorescence microscope, the structured-illumination module comprising: a structured-illumination-module frame; a beam-alignment module including a central tilt mirror coupled to an underside of a top horizontal plate of the structured-illumination-module frame; a set of directional mirrors, one of which receives, at a given point in time, input, polarized, coherent light reflected from the central tilt mirror; three sets of beam splitters, on three arms of the structured-illumination-module frame, the each splits an incident illumination beam, reflected to the set of beam splitters from a directional mirror of the set of directional mirrors, into a coherent beam triplet; and a phase-shift module that receives a beam triplet, at a given point in time, generated by one of the sets of beam splitters and reflected from the beam-alignment module and that introduces a desired relative phase relationship among the beams of the beam triplet.

* * * * *